United States Patent
Mehta et al.

(10) Patent No.: US 11,701,402 B2
(45) Date of Patent: Jul. 18, 2023

(54) POLYPHARMACEUTICAL DRUG COMPOSITIONS AND RELATED METHODS

(71) Applicant: Aveta Biomics, Inc., Bedford, MA (US)

(72) Inventors: Parag G. Mehta, Burlington, MA (US); Sharmila Mudgal, Lexington, MA (US); Lal Hingorani, Maharashtra (IN); Luis Z. Avila, Arlington, MA (US)

(73) Assignee: Aveta Biomics, Inc., Bedford, MA (US)

( * ) Notice: Subject to any disclaimer, the term of this patent is extended or adjusted under 35 U.S.C. 154(b) by 22 days.

(21) Appl. No.: 17/044,696

(22) PCT Filed: Apr. 2, 2019

(86) PCT No.: PCT/US2019/025465
§ 371 (c)(1),
(2) Date: Oct. 1, 2020

(87) PCT Pub. No.: WO2019/195349
PCT Pub. Date: Oct. 10, 2019

(65) Prior Publication Data
US 2021/0252097 A1     Aug. 19, 2021

Related U.S. Application Data

(60) Provisional application No. 62/651,683, filed on Apr. 2, 2018.

(51) Int. Cl.
*A61K 36/9066* (2006.01)
*A61K 31/12* (2006.01)
*A61K 47/44* (2017.01)
*A61K 45/06* (2006.01)
*A61P 35/00* (2006.01)

(52) U.S. Cl.
CPC .......... *A61K 36/9066* (2013.01); *A61K 31/12* (2013.01); *A61K 45/06* (2013.01); *A61K 47/44* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 2008/0193573 A1* | 8/2008 | Gow | A23L 33/105 426/655 |
| 2008/0233218 A1 | 9/2008 | Newmark et al. | |
| 2016/0151440 A1 | 6/2016 | Gopi | |
| 2016/0235803 A1 | 8/2016 | Thakkar | |
| 2016/0256513 A1 | 9/2016 | May et al. | |

FOREIGN PATENT DOCUMENTS

| | | |
|---|---|---|
| WO | WO 2015/076430 A1 | 5/2015 |
| WO | WO 2019/195349 | 10/2019 |

OTHER PUBLICATIONS

Thvar "Characterization of the Purity of Curcumin Extraction : Comparative study of UV Spectrophotometry and High Performance Liquid Chromatography from a Field Application Perspective" published 2012.*
Dielectric Constant.*
Miller's Home.*
Chang, et al., Immunomodulation of Curcumin on Adoptive Therapy with T Cell Functional Imaging in Mice, Cancer Prevention Research, vol. 5, No. 3, Mar. 2012, pp. 444-452.
International Search Report issued in International Application No. PCT/US2019/025465 dated Jun. 14, 2019.

* cited by examiner

*Primary Examiner* — Danah Al-Awadi
(74) *Attorney, Agent, or Firm* — Morse, Barnes-Brown & Pendleton, P.C.; Stanley F. Chalvire, Esq.; Erin E Bryan, Esq.

(57) ABSTRACT

Disclosed are compositions and methods for treating or ameliorating the symptoms of cancer (e.g., oral cancer) by using a poly-pharmaceutical drug, whose composition consists of relationally optimized ratios of bioactive compounds to enhance their pharmacological characteristics.

17 Claims, 12 Drawing Sheets

Post AV1016 Treatment Immunofluorescence

Pre-Treatment Immunofluorescence

Tumor (asterisk surrounded by a mix of CD4 (orange arrow) and CD8 (teal arrows) positive cells). Rare PD-L1 positive cells are also present (red arrow). PD-1 = Green, PD-L1 = Red, CD4 = Orange, CD8 = Cyan, Nucleus = DAPI (dark blue). Stage 4 Floor of the Mouth Treatment Naïve Cancer Patient

POLYPHARMACEUTICAL DRUG COMPOSITIONS AND RELATED METHODS

RELATED APPLICATIONS PARAGRAPH

This application is a national stage filing under 35 U.S.C. 371 of International Application No. PCT/US2019/025465, filed Apr. 2, 2019, which claims claim the benefit of U.S. Provisional Application No. 62/651,683, filed Apr. 2, 2018. The entire teachings of the above applications are incorporated herein by reference. International Application No. PCT/US2019/025465 was published under PCT Article 21(2) in English.

BACKGROUND OF THE INVENTION

Presently available cancer therapies generally involve multiple treatment modalities, which may include cytotoxic drugs, more targeted therapeutics, biologics, and immunotherapeutics. Although many cancers initially respond dramatically to these drugs, in a majority of cases the evolutionary pro-survival mechanisms of these cancers create adaptive responses that circumvent the mechanism of action of these drugs. This leads to drug resistance and/or recurrence with no real survival benefit to patients.

A single-agent drug that can effectively address multiple molecular events in a tumor is virtually impossible given that there are many biochemical species that contribute to the disease phenotype and thus different molecular targets require a diversity of drug molecules in order to modulate the biochemical response. Therefore, in the treatment of many diseases, particularly in cases of cancer, it is fairly common to have a cocktail of drugs wherein different drug molecules work through different mechanisms and on different targets. However, one of the most common problems associated with such cocktails is that the number of unique molecules in the cocktail is limited to a handful because interactions among these molecules often lead to undesirable, adverse effects. The second concern is that the molecules in the "artificially" combined drug cocktail often lack true synergy in its pharmacological activity in order to provide a durable clinical response, free from resistance to drugs and/or prevention of recurrence.

Needed are new therapeutics, compositions, and methods of making and/or using poly-pharmaceutical drugs containing multiple compounds that are capable of pleiotropic and truly synergistic action to address vast molecular heterogeneity of the tumor and the tumor microenvironment.

SUMMARY OF THE INVENTION

Disclosed herein are therapeutic and pharmaceutical compositions and related methods of use or manufacture of plant-derived poly-pharmaceutical drugs. The bioactive compounds that comprise the compositions disclosed herein are, in certain embodiments, the metabolites (e.g., the isolated metabolites) produced by plants under intense selection, both for targeting selectivity and high potency through millions of years of evolution.

Nature has produced a chemical library unmatched by any combinatorial library produced by a human. The inventions disclosed herein further recognize that the naturally occurring composition of these poly-pharmaceuticals extracted from the plants requires "re-optimization" to address therapeutic challenges that are unique only to humans, including cancer.

In certain aspects, disclosed herein are pharmaceutical compositions comprising: (a) one or more high polarity compounds isolated from *Curcuma longa* and selected from the group consisting of peptides, polysaccharides, and proteins; (b) one or more medium polarity compounds selected from the group consisting of polyphenols, curcumin, demethoxycurcumin, and bisdemethoxycurcumin; and (c) one or more non-polar compounds selected from the group consisting of terpenoids, ar-turmerone, α-turmerone, and β-turmerone; wherein the composition comprises a ratio of the high polarity compounds, medium polarity compounds and non-polar compounds selected from the group consisting of about [1]:[1]:[1] by weight and about [3]:[6]:[1] by weight.

In some aspects, the disclosure relates to pharmaceutical compositions comprising: (a) one or more fractions isolated from *Curcuma longa*, wherein the fractions comprise one or more extracts of the *Curcuma longa* enriched with (i) one or more high polarity compounds selected from the group consisting of peptides, polysaccharides, and proteins; (ii) one or more medium polarity compounds selected from the group consisting of polyphenols, curcumin, demethoxycurcumin, and bisdemethoxycurcumin; and (iii) one or more non-polar compounds selected from the group consisting of terpenoids, ar-turmerone, α-turmerone, and β-turmerone; and (b) one or more pharmaceutical excipients (e.g., one or more of the pharmaceutical excipients described in U.S. Pat. No. 9,913,873, the entire contents of which are incorporated by reference herein).

In some embodiments, the one or more high polarity extracts comprise between about 5-60% w/w (e.g., 20-60% w/w) of the composition or between about 10-40% w/w (e.g., 25-40% w/w) of the composition. In some embodiments, the one or more medium polarity extracts comprise between about 20-95% w/w (e.g., 26-95% w/w) of the composition or between about 50-80% w/w (e.g., 50-70% w/w) of the composition. In some embodiments, the one or more non-polar extracts comprise between about 5-50% w/w of the composition or between about 5-15% w/w of the composition. In some embodiments, the one or more high polarity extracts are obtained by extracting the botanical material using a solvent system that has a dielectric constant less than 25 or a relative polarity greater than about 0.6. In some embodiments, the one or more high polarity extracts comprise polysaccharides, peptides, and proteins (e.g., polysaccharides, peptides, and proteins isolated or extracted from *Curcuma longa*). In some embodiments, the one or more medium polarity extracts are obtained by extracting the botanical material using a solvent system that has a dielectric constant between 5 and 25 or a relative polarity between about 0.25-0.6. In some embodiments, the one or more medium polarity extracts comprise curcumin, demethoxycurcumin, and bisdemethoxycurcumin. In some embodiments, the one or more low polarity or non-polar extracts are obtained by extracting the botanical material using the solvent system that has dielectric constant less than 5 or a relative polarity less than about 0.25. In some embodiments, the one or more non-polar extract comprises terpenoids, ar-turmerone, α-turmerone, and β-turmerone.

In some embodiments, the composition is formulated for oral administration, buccal administration, sublingual administration and/or transdermal administration to a subject. In some embodiments, one or more pharmaceutical excipients are selected from the group consisting of diluents, disintegrants, carriers (e.g., hydrogel matrix), binders, adhesives, surfactants, lubricants, solvents, permeation enhancers (e.g., menthol, surfactants, alcohols, polyols, polyether, cyclodextrin, and fatty acid derivatives), plasticizers, gelling agents, water, release agents, flavorings, sweeteners, preservatives, and mixtures thereof. In some embodiments, one or more pharmaceutical excipients are selected from the group consisting of glycerin, gelatin, water, saline, dextrose, glycerol, ethanol, and combinations thereof. In certain aspects, the compositions disclosed herein are formulated as a soft pastille, as described in U.S. Pat. No. 9,913,873, the entire contents of which are incorporated by reference herein. In some embodiments, the pharmaceutical excipients comprise a carrier (e.g., a fish oil carrier).

In some embodiments, one or more of the high polarity extracts, medium polarity extracts, and non-polar extracts are micronized. In some embodiments, the *Curcuma longa* extracts do not comprise one or more of insoluble natural polymers such as cellulose and lignin materials.

In some embodiments, the composition comprises about 11-15% w/w (e.g., 11% w/w) of the high polarity polysaccharides, about 41-44% w/w (e.g., 44% w/w) of the medium polarity compound curcumin, and about 3-4% w/w (e.g., 4% w/w) of the non-polar compound ar-tumerone. In some embodiments, the composition comprises a ratio of about [3]:[6]:[1] of high polarity extracts, medium polarity extracts and non-polar extracts, respectively. In some embodiments, the composition comprises a ratio of about [1]:[1]:[1] of high polarity extracts, medium polarity extracts and non-polar extracts, respectively.

In some embodiments, the composition further comprises an effective amount of one or more chemotherapeutic agents. Examples of chemotherapeutic agents include, but are not limited to, antimetabolite agents, antibiotic-type agents, alkylating agents, hormonal agents, immunological agents, interferon-type agents, matrix metalloproteinases, and superoxide dismutase mimics.

In certain embodiments of the foregoing methods, the composition is administered in combination with an immunotherapy agent. For example, in certain embodiments, the compositions disclosed herein are administered to a subject in combination with an immunotherapy agent selected from the group consisting of checkpoint inhibitors, checkpoint blockers, vaccines and CAR-T cells.

In some aspects, the disclosure relates to methods of treating cancer or a pre-cancerous condition (e.g., leukoplakia), the method comprising administering an effective amount of the composition as described herein to a subject in need thereof, thereby treating cancer or pre-cancerous condition. In some embodiments, cancer is oral squamous cell carcinoma. In some embodiments, the pre-cancerous condition is leukoplakia. In some embodiments, the subject is a mammal (e.g., a human).

In some embodiments, an effective amount of the composition comprises at least about 200-600 mg per day. In some embodiments, the composition is administered to the subject (e.g., a human subject) at least once daily, at least twice daily, at least three times daily, or at least four times daily.

In some aspects, the disclosure relates to methods of treating oral or oropharyngeal squamous cell carcinoma in a subject in need thereof, such methods comprising a step of administering a pharmaceutical composition to the subject, wherein the composition comprises: (a) one or more fractions isolated from *Curcuma longa*, wherein the fractions comprise one or more extracts of the *Curcuma longa* enriched with (i) one or more high polarity compounds selected from the group consisting of proteins, polysaccharides, and peptides; (ii) one or more medium polarity compounds selected from the group consisting of polyphenols, curcumin, demethoxycurcumin, bisdemethoxycurcumin and combinations thereof; and (iii) one or more non-polar compounds selected from the group consisting of terpenoids, ar-turmerone, α-turmerone, β-turmerone and combinations thereof; and (b) one or more pharmaceutical excipients.

In certain aspects, the disclosure relates to methods of treating oral squamous cell carcinoma in a subject in need thereof, such methods comprising a step of administering a pharmaceutical composition to the subject, wherein the composition comprises: (a) one or more high polarity compounds isolated from *Curcuma longa* and selected from the group consisting of proteins, polysaccharides, and peptides; (b) one or more medium polarity compounds selected from the group consisting of polyphenols, curcumin, demethoxycurcumin, and bisdemethoxycurcumin; and (c) one or more non-polar compounds selected from the group consisting of terpenoids, ar-turmerone, α-turmerone, and β-turmerone; wherein the composition comprises a ratio of the high polarity compounds, medium polarity compounds and non-polar compounds selected from the group consisting of about [1]:[1]:[1] by weight and about [3]:[6]:[1] by weight.

In certain aspects, the disclosure relates to methods of treating or preventing a pre-cancerous condition in a subject in need thereof. For example, in certain embodiments, the methods and compositions disclosed herein may be used therapeutically or prophylactically to treat or prevent a pre-cancerous condition. Such methods comprise a step of administering a pharmaceutical composition to the subject, wherein the composition comprises: (a) one or more high polarity compounds isolated from *Curcuma longa* and selected from the group consisting of proteins, polysaccharides, and peptides; (b) one or more medium polarity compounds selected from the group consisting of polyphenols, curcumin, demethoxycurcumin, and bisdemethoxycurcumin; and (c) one or more non-polar compounds selected from the group consisting of terpenoids, ar-turmerone, α-turmerone, and β-turmerone; wherein the composition comprises a ratio of the high polarity compounds, medium polarity compounds and non-polar compounds selected from the group consisting of about [1]:[1]:[1] by weight and about [3]:[6]:[1] by weight. In certain aspects, the pre-cancerous condition is leukoplakia.

In some embodiments of the foregoing methods, the one or more high polarity extracts comprise between about 20-60% w/w of the composition or between about 25-40% w/w of the composition. In some embodiments of the foregoing methods, the one or more medium polarity extracts comprise between about 25-80% w/w of the composition or between about 50-70% w/w of the composition. In some embodiments of the foregoing methods, the one or more non-polar extracts comprise between about 5-50% w/w of the composition or between about 5-15% w/w of the composition.

Also disclosed herein are methods of promoting or increasing T-cell infiltration in a tumor of a subject (e.g., converting a tumor from "cold" to "hot") thereby improving or increasing the sensitivity of such tumor to, for example, chemotherapy and/or immunotherapy. In certain aspects, such methods comprise a step of administering a pharmaceutical composition to the subject, wherein the composition comprises: (a) one or more high polarity compounds isolated from *Curcuma longa* and selected from the group consisting of proteins, polysaccharides, and peptides; (b) one or more medium polarity compounds selected from the group consisting of polyphenols, curcumin, demethoxycurcumin, and bisdemethoxycurcumin; and (c) one or more non-polar compounds selected from the group consisting of terpenoids, ar-turmerone, α-turmerone, and β-turmerone; wherein the composition comprises a ratio of the high polarity compounds, medium polarity compounds and non-polar compounds selected from the group consisting of about [1]:[1]:[1] by weight and about [3]:[6]:[1] by weight, and thereby promoting or increasing the infiltration of T-cells in the tumor or tumor microenvironment.

In some embodiments of the foregoing methods, the one or more high polarity extracts are obtained by isolating or extracting the botanical material using a solvent system that has a dielectric constant less than 25 or have a relative polarity greater than about 0.6. In some embodiments, the one or more high polarity extracts comprise polysaccharides, and nitrogen containing compounds (e.g., peptides and proteins). In some embodiments, one or more medium polarity extracts are obtained by isolating or extracting the botanical material using a solvent system that has a dielectric constant between 5 and 25 or have a relative polarity between about 0.25-0.6. In some embodiments, the one or more medium polarity extracts comprise curcumin, demethoxycurcumin, and bisdemethoxycurcumin. In some embodiments, one or more low polarity or non-polar extracts are obtained by isolating or extracting the botanical material using a solvent system that has dielectric constant less than 5 or have a relative polarity less than about 0.25. In some embodiments, the one or more non-polar extracts comprise terpenoids, ar-turmerone, α-turmerone, and β-turmerone.

In some embodiments of the foregoing methods, the composition is formulated for oral administration, buccal administration, sublingual administration or transdermal administration to a subject. In some embodiments, the one or more pharmaceuticals excipient are selected from the group consisting of diluents, disintegrants, carriers (e.g., hydrogel matrix), binders, adhesives, surfactants, lubricants, solvents, permeation enhancers (e.g., menthol, surfactants, alcohols, polyols, polyether, cyclodextrin, and fatty acid derivatives), plasticizers, gelling agents, water, release agents, flavorings, sweeteners, preservatives, and mixtures thereof. In some embodiments, one or more pharmaceutical excipients are selected from the group consisting of glycerin, gelatin, water, saline, dextrose, glycerol, ethanol, and combinations thereof. In some embodiments, the pharmaceutical excipient comprises a carrier (e.g., a fish oil).

In some embodiments of the foregoing methods, one or more of the high polarity compounds, medium polarity compounds and non-polar compounds are micronized. In some embodiments, the *Curcuma longa* extracts do not comprise one or more of insoluble natural polymers, such as cellulose and lignin materials.

In some embodiment of the foregoing methods, the composition comprises about 11-15% w/w (e.g., 15% w/w) of high polarity polysaccharides, about 41-44% w/w (e.g., 41% w/w) of medium polarity compound curcumin, and about 3-4% w/w (e.g., 3% w/w) of the non-polar compound ar-tumerone. In some embodiments of the foregoing methods, the composition comprises a ratio of about [3]:[6]:[1] by weight of the high polarity compounds, medium polarity compounds and non-polar compounds. In some embodiments of the foregoing methods, the composition comprises a ratio of about [1]:[1]:[1] by weight of the high polarity compounds, medium polarity compounds and non-polar compounds.

In some embodiments, the composition further comprises an effective amount of one or more chemotherapeutic agents. Examples of chemotherapeutic agents include, but are not limited to, antimetabolite agents, antibiotic-type agents, alkylating agents, hormonal agents, immunological agents, interferon-type agents, matrix metalloproteinases, and superoxide dismutase mimics.

In certain embodiments of the foregoing methods, the composition is administered in combination with an immunotherapy agent. For example, in certain embodiments, the compositions disclosed herein are administered to a subject in combination with an immunotherapy agent selected from the group consisting of checkpoint inhibitors, checkpoint blockers, vaccines and CAR-T cells.

In some embodiments, the high polarity compounds are extracted from the *Curcuma longa* using a solvent having a dielectric constant greater than about 25 (e.g., formamide, dimethylformamide (DMF), dimethylacetamide (DMAC), methanol, ethanol, water, acetonitrile, and combinations thereof). In some embodiments, the medium polarity compounds are extracted from the *Curcuma longa* using a solvent having a dielectric constant between about 5-25 (e.g., ethyl acetate, acetone, 1,2-dichloroethane, THF, isopropyl alcohol, pyridine, ethyl 1,2 dimethylethane, chlorobenzene, and combinations thereof). In some embodiments, the non-polar compounds are extracted from the *Curcuma longa* using a solvent having a dielectric constant less than about 5 (e.g., carbon disulfide, carbon tetrachloride, supercritical $CO_2$, cyclohexane, diethyl ether, trichloroethylene, O-xylene, and combinations thereof).

The above discussed, and many other features and attendant advantages of the present invention will become better understood by reference to the following detailed description of the invention when taken in conjunction with the accompanying examples.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE INVENTION

Figure 1:
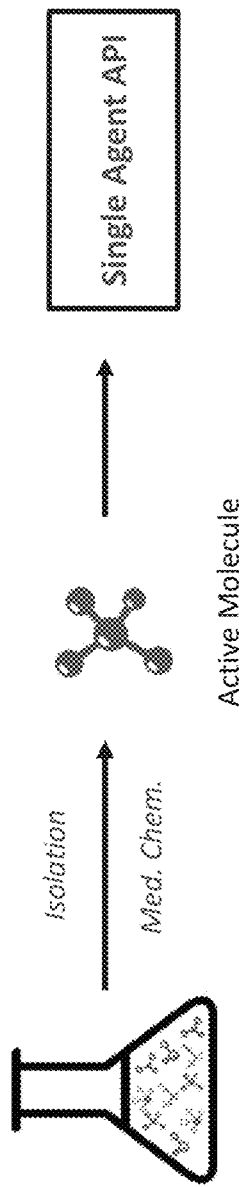
FIG. 1 depicts a schematic of a process for developing a drug from a plant source. The schematic demonstrates the isolation and purification of an active molecule from a plant source and the use of that active molecule in forming a single agent drug (e.g., a silver bullet).

Disclosed herein are compositions and related methods of use or manufacture of poly-pharmaceutical drugs that consist of combinations of different physical extracts of *Curcuma longa*. In certain embodiments, the inventions disclosed herein concern a two-step process of preparing the compositions disclosed herein. In the first step, the selective enrichment and/or depletion of various classes of compounds present in *C. longa* using various methods of extraction takes place. These extraction processes are based on the use of solvent systems of varying polarity, as further described herein. For example, in certain aspects, a low or non-polar extract is obtained by extracting the botanical material (e.g., *Curcuma longa*) using a solvent system that has a dielectric constant less than about 5 or relative polarity of less than about 0.2. In some embodiments, a medium polarity extract is obtained by extracting the botanical material (e.g., *Curcuma longa*) using a solvent system that has a dielectric constant between about 5 and 25 and/or a relative polarity equal to or between about 0.25 and 0.6. In certain embodiments, a high polarity extract is obtained using a solvent system that has a dielectric constant greater than about 25 and/or a relative polarity greater than about 0.6

In the second step, these extracts are combined to create an optimized formulation based on in-vitro and/or in-vivo evaluations, thereby creating an artificial ratio of the compounds that is unique relative to the ratios of such compounds that are observed in the natural plant. The reformulation results in improved pharmacological activity, pharmacokinetic (PK) activity and/or improved pharmacodynamic (PD) activity of such compounds.

The objective of creating a new polypharmaceutical composition, where multiple molecules act synergistically is to provide a superior pharmacological response.

The inventions disclosed herein also describe the use of the polypharmaceutical drugs for the treatment of cancer (e.g., oral squamous cell cancer (OSCC)) or pre-cancerous conditions (e.g., leukoplakia), including the use of biomarkers to gauge the efficacy of the therapy. In certain aspects, the methods and compositions disclosed herein are useful for the treatment or prevention of oral cancers (e.g., OSCC). In certain aspects, the methods and compositions disclosed herein are useful for the treatment or prevention of pre-cancerous conditions, such as leukoplakia. The inventions disclosed herein also describe formulations for targeted and controlled delivery of the polypharmaceutical drugs, in particular, into the local oral cavity and into the systemic circulation of a subject via mucosal absorption (e.g., such inventions may be formulated as a pastille as described in U.S. Pat. No. 9,913,873, the entire contents of which are incorporated by reference herein).

The pharmaceutical compositions described herein comprise a combination of extracts containing low or non-polar compounds, medium polarity compounds, and highly polar compounds. As used herein, a "solvent system" refers to either a single solvent or a combination of solvents. As used herein, a "low polarity" or "non-polar" compound refers to the compound(s) extracted using a solvent system having a dielectric constant of less than about 5 and the relative polarity value of less than about 0.2. Exemplary low polarity or non-polar compounds may be selected from the group consisting of terpenoids, ar-turmerone, α-turmerone, β-turmerone, and combinations thereof. As used herein, a "medium polarity" compound refers to the compound(s) being extracted using a solvent system having a dielectric constant between about 5 to 25 and having the relative polarity value between about 0.25 and 0.6. Exemplary medium polarity compounds may be selected from the group consisting of curcumin, demethoxycurcumin, bisdemethoxycurcumin, and combinations thereof. As used herein, a "highly polar" or "high polarity" compound refers to the compound(s) extracted using a solvent system that has a dielectric constant greater than about 25 and the relative polarity of greater than about 0.6. Exemplary high polarity compounds may be selected from the group consisting of proteins, polysaccharides, peptides, and combinations thereof (e.g., proteins, polysaccharides, peptides isolated from *Curcuma longa*). Additional examples of non-polar or low polarity compounds, medium polarity compounds, and high polarity compounds are described by Li et al., Chemical Composition and Product Quality Control of Turmeric (*Curcuma longa*), Pharmaceutical Crops, 2011, 2:28-54, the entire contents of which are incorporated herein by reference.

The high polarity compounds of the pharmaceutical composition may comprise between about 5% to 60% w/w of the composition, 5% to 50% w/w of the composition, or alternatively 10% to 40% w/w of the composition. The medium polarity compounds of the pharmaceutical composition may comprise between about 20% to 95% w/w of the composition, 30% to 80% w/w of the composition, or alternatively 50% to 80% w/w of the composition. The non-polar compounds of the pharmaceutical composition may comprise between about 5% to 50% w/w of the composition, 5% to 40% of the composition, or alternatively 5% to 15% w/w of the composition. In some aspects, a pharmaceutical composition comprises about 30% w/w of the composition high polarity compounds, about 61% w/w of the composition medium polarity compounds, and about 9% w/w of the composition non-polar compounds. In other aspects, a pharmaceutical composition comprises about 33% w/w of the composition high polarity compounds, about 33% w/w of the composition medium polarity compounds, and about 33% w/w of the composition non-polar compounds.

In some embodiments, the compositions disclosed herein comprise a ratio of about [3]:[6]:[1] of high polarity extracts, medium polarity extracts and non-polar extracts, respectively. In some embodiments, the compositions disclosed herein comprise a ratio of about [1]:[1]:[1] of high polarity extracts, medium polarity extracts and non-polar extracts, respectively.

In some aspects, the composition comprises a combination of extracts containing low or non-polar compounds in the range of about 3% to 100% w/w of the composition (e.g., about 10% w/w), medium polarity compounds in the range of about 3% to 95% w/w of the composition (e.g., about 60% w/w), and highly polar compounds in the range of about 3% to 55% w/w of the composition (e.g., about 30% w/w). In certain aspects, the composition comprises a combination of extracts containing low or non-polar compounds in the range of about 4% to 50% w/w of the composition (e.g., about 33% w/w), medium polarity compounds in the range of about 5% to 60% w/w of the composition (e.g., about 33% w/w), and highly polar compounds in the range of about 10% to 40% w/w of the composition (e.g., about 33% w/w).

One or more high polarity compounds may be extracted using a solvent system that has a relative polarity greater than about 0.6. In some aspects, one or more medium polarity compounds may be extracted using a solvent system that has a relative polarity between about 0.25 and 0.6. One or more non-polar or low polarity compounds may be extracted using a solvent system that has a relative polarity of less than about 0.25. As used herein, "relative polarity" refers to the values for relative polarity normalized from measurements of solvent shifts of absorption spectra and are described in Christian Reichardt, *Solvents and Solvent Effects in Organic Chemistry*, Wiley-VCH Publishers, 3$^{rd}$ ed., 2003, the contents of which are incorporated herein by reference.

The pharmaceutical composition disclosed herein may comprise a ratio of high polarity compounds, medium polarity compounds, and non-polar compounds. In some aspects, the pharmaceutical composition comprises a [3]:[6]:[1] ratio of high polarity compounds, medium polarity compounds, and non-polar compounds. In other aspects, the pharmaceutical composition comprises a [1]:[1]:[1] ratio of high polarity compounds, medium polarity compounds, and non-polar compounds.

In some aspects, the pharmaceutical compositions disclosed herein comprise one or more fractions isolated from *Curcuma longa* (e.g., one, two, three, four, five, six or more fractions). The fractions may comprise one or more extracts of the *C. longa* enriched with one or more high polarity compounds, one or more medium polarity compounds, and one or more non-polar compounds. In certain embodiments, the *C. longa* extracts do not comprise one or more of water-insoluble natural polymers, such as lignin and cellulose.

In some aspects, the high polarity compounds are extracted from the *C. longa* using a solvent having a dielectric constant greater than about 25. The solvent having a dielectric constant greater than about 25 may be selected from the group consisting of formamide, dimethylformamide (DMF), dimethylacetamide (DMAC), methanol, ethanol, water, acetonitrile, and combinations thereof. In certain aspects, the solvent having a dielectric constant greater than about 25 is water. In some aspects, the medium polarity compounds are extracted from the *C. longa* using a solvent having a dielectric constant between about 5 and 25 or relative polarity value between about 0.25 and 0.6. The solvent having a dielectric constant between about 5 and 25 or relative polarity value between about 0.25 and 0.6 may be selected from the group consisting of ethyl acetate, acetone, 1,2-dichloroethane, THF, isopropyl alcohol, pyridine, ethyl benzoate, 1,2-dimethoxyethane, chlorobenzene, and combinations thereof. In certain aspects, the solvent having a dielectric constant between about 5 and 25 or relative polarity value between about 0.25 and 0.6 is ethyl acetate. In some aspects, the non-polar or low polarity compounds are extracted from the *C. longa* using a solvent having a dielectric constant less than about 5 or relative polarity value of less than about 0.2. The solvent having a dielectric constant less than about 5 may be selected from the group consisting of carbon disulfide, carbon tetrachloride, supercritical $CO_2$, cyclohexane, diethyl ether, trichloroethylene, O-xylene, and combinations thereof. In certain aspects the solvent having a dielectric constant less than about 5 or relative polarity value of less than about 0.2 is $CO_2$.

High polarity compounds may be selected from the group consisting of proteins, polysaccharides (e.g., hydrolyzable polysaccharides), and peptides. Medium polarity compounds may be selected from the group consisting of polyphenols, such as curcumin, demethoxycurcumin, bisdemethoxycurcumin and combinations thereof. Non-polar or low polarity compounds may be selected from the group consisting of terpenoids, ar-turmerone, α-turmerone, β-turmerone and combinations thereof. In some aspects, one or more of the high polarity compounds, medium polarity compounds, and non-polar compounds are micronized.

The pharmaceutical composition may further include one or more pharmaceutical excipients. The pharmaceutical excipient may be selected from the group consisting of plasticizer, gelling agent, water, release agent, flavoring, sweetener, preservative, diluents, disintegrants, carriers (e.g., a hydrogel matrix), binders, adhesives, surfactants, lubricants, solvents, permeation enhancers (e.g., menthol, surfactants, alcohols, polyols, polyethers, cyclodextrin, fatty acid derivatives), and mixtures thereof. Suitable excipients may include, for example, glycerin, gelatin, water, saline, dextrose, glycerol, ethanol or the like, and combinations thereof. In certain aspects, the compositions disclosed herein may comprise one or more of the pharmaceutical excipients disclosed in U.S. Pat. No. 9,913,873, the entire contents of which are incorporated by reference herein.

The pharmaceutical compositions described herein demonstrate improved pharmacologic, pharmacokinetic (PK) and/or improved pharmacodynamic (PD) properties relative to a naturally occurring *Curcuma longa*. In some aspects the PK value is influenced by the delivery method of the pharmaceutical composition. Further, the pharmaceutical compositions described herein demonstrate improved efficacy relative to naturally occurring *Curcuma longa*. It is generally understood that the various polar compounds of the pharmaceutical composition demonstrate synergy, thereby contributing to the benefits identified.

Also disclosed herein are methods of treating cancer or pre-cancerous conditions in a subject, such methods comprising the administration of the compositions disclosed herein to the subject. In some embodiments, a method of treating cancer or pre-cancerous conditions includes administering to the subject in need thereof an effective amount of the pharmaceutical composition described herein, thereby treating cancer. In some aspects, cancer is oral cancer (e.g., oral squamous cell carcinoma). In some aspects, cancer is oral cancer is Glioblastoma, lung cancer, colon cancer and pancreatic cancer. In some aspects, the condition is pre-cancerous (e.g., a pre-cancerous condition, such as leukoplakia) where the methods and compositions disclosed herein may be used therapeutically and/or prophylactically.

In certain embodiments, the compositions disclosed herein are useful for promoting and/or increasing T-cell infiltration in a tumor of a subject. For example, disclosed herein are methods of converting a tumor from "cold" to "hot," thereby improving or increasing the sensitivity of such tumor to, for example, chemotherapy and/or immunotherapy. In certain aspects, such methods comprise a step of administering a pharmaceutical composition to the subject, wherein the composition comprises: (a) one or more high polarity compounds isolated from *Curcuma longa* and selected from the group consisting of proteins, polysaccharides, and peptides; (b) one or more medium polarity compounds selected from the group consisting of polyphenols, curcumin, demethoxycurcumin, and bisdemethoxycurcumin; and (c) one or more non-polar compounds selected from the group consisting of terpenoids, ar-turmerone, α-turmerone, and β-turmerone; wherein the composition comprises a ratio of the high polarity compounds, medium polarity compounds and non-polar compounds selected from the group consisting of about [1]:[1]:[1] by weight and about [3]:[6]:[1] by weight, and thereby promoting or increasing the infiltration of T-cells in the tumor or tumor microenvironment of a subject.

As used herein, a "subject" means a human or animal (e.g., a primate). Usually, the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient", "individual" and "subject" are used interchangeably herein. Preferably, the subject is a mammal. The mammal can be a human, non-human primate, mouse, rat, dog, cat, horse, or cow, but are not limited to these examples. In addition, the methods described herein can be used to treat domesticated animals and/or pets. A subject can be male or female. A subject can be one who has been previously diagnosed with or identified as suffering from or having a condition in need of treatment or one or more complications related to such a condition, and optionally, but need not have already undergone treatment for a condition or one or more complications related to the condition. Alternatively, a subject can also be one who has not been previously diagnosed as having a condition in need of treatment or one or more complications related to such a condition. Rather, a subject can include one who exhibits one or more risk factors for a condition or one or more complications related to a condition. A "subject in need" of treatment for a particular condition can be a subject having that condition, diagnosed as having that condition, or at increased risk of developing that condition relative to a given reference population.

An effective amount of the pharmaceutical composition administered to a subject comprises at least about 100-600 mg per day, and in some aspects at least about 200-500 mg per day of the active extracts or ingredients. This amount comprises the combined mass of the high polarity compounds, the medium polarity compounds, and the low or non-polarity compounds. In some aspects the pharmaceutical composition comprises the combined mass of the high polarity compounds, the medium polarity compounds, and the low or non-polarity compounds in a 3:6:1 ratio. In some aspect the pharmaceutical composition comprises the combined mass of the high polarity compounds, the medium polarity compounds, and the low or non-polarity compounds in a 1:1:1 ratio. In some aspects, the pharmaceutical composition is administered to the subject (e.g., administered buccally or sublingually) at least one, at least two, at least three, at least four, at least five times daily or more. In some aspects 100 mg of the pharmaceutical composition is administered to a subject one, two, three, four, or five times daily. In certain aspects 100 mg of the high, medium and low polarity compound (e.g., at 3:6:1 ratio, respectively) is administered to a subject twice a day.

In some embodiments, a method of treating cancer (e.g., oral squamous cell carcinoma) in a subject in need thereof is disclosed. The method comprises a step of administering a pharmaceutical composition to the subject, wherein the composition comprises (a) one or more fractions isolated from *Curcuma longa*, wherein the fractions comprise one or more extracts of the *C. longa* enriched with (i) one or more high polarity compounds selected from the group consisting of proteins, polysaccharides, and peptides; (ii) one or more medium polarity compounds selected from the group consisting of polyphenols, curcumin, demethoxycurcumin, bisdemethoxycurcumin and combinations thereof; and (iii) one or more non-polar compounds selected from the group consisting of terpenoids, ar-turmerone, α-turmerone, β-turmerone and combinations thereof; and (b) one or more pharmaceutical excipients (e.g., one or more of the pharmaceutical excipients described in U.S. Pat. No. 9,913,873, the entire contents of which are incorporated by reference herein).

In some embodiments, the pharmaceutical composition is formulated for administration to a subject (e.g., oral, buccal, transdermal or sublingual administration). Pharmaceutical compositions comprise one or more agents or compositions that have therapeutic utility, and a pharmaceutically acceptable carrier (e.g., a carrier that facilitates delivery of agents or compositions). Agents and pharmaceutical compositions disclosed herein may be administered by any suitable means such as orally, intranasally, subcutaneously, intramuscularly, intravenously, intra-arterially, parenterally, intraperitoneally, intrathecally, intratracheally, ocularly, sublingually, vaginally, rectally, dermally, or as an aerosol. Depending upon the type of condition (e.g., cancer) to be treated, compounds and composition of the invention may, for example, be inhaled, ingested or administered by systemic routes. Thus, a variety of administration modes, or routes, are available. The particular mode selected will typically depend on factors such as the particular compound selected, the particular condition being treated and the dosage required for therapeutic efficacy. The methods described herein, generally speaking, may be practiced using any mode of administration that is medically acceptable, meaning any mode that produces acceptable levels of efficacy without causing clinically unacceptable adverse effects. Exemplary methods for administering the pharmaceutical composition to the subject include oral, buccal, sublingual and/or transdermal administration.

The pharmaceutical compositions described herein may be delivered to a subject by means of a pharmaceutically acceptable carrier (e.g., a fish oil carrier). Such carriers are well known in the art and can be one or more compatible solid or liquid vehicles, fillers, diluents, or encapsulating substances which are suitable for administration to a human or non-human animal. In preferred embodiments, a pharmaceutically acceptable carrier is a non-toxic material that does not interfere with the effectiveness of the biological activity of the active ingredients. The term "compatible," as used herein, means that the components of the pharmaceutical compositions are capable of being comingled with an agent, and with each other, in a manner such that there is no interaction which would substantially reduce the pharmaceutical efficacy of the pharmaceutical composition under ordinary use situations. Pharmaceutically acceptable carriers should be of sufficiently high purity and sufficiently low toxicity to render them suitable for administration to the human or non-human animal being treated.

Some examples of substances which can serve as pharmaceutically acceptable carriers are pyrogen-free water; isotonic saline; phosphate buffer solutions; sugars such as lactose, glucose, and sucrose; starches such as corn starch and potato starch; cellulose and its derivatives, such as sodium carboxymethylcellulose, ethylcellulose, cellulose acetate, powdered tragacanth, malt; gelatin, talc, stearic acid, magnesium stearate, calcium sulfate, vegetable oils such as peanut oil, cottonseed oil, sesame oil, olive oil, corn oil, oil of *Theobroma*, fish oil such as those containing long-chain omega-3 polyunsaturated fatty acids (PUFA), polyols such as propylene glycol, glycerin, sorbitol, mannitol, and polyethylene glycol, sugar, alginic acid, cocoa butter (suppository base), emulsifiers such as the Tweens as well as other non-toxic compatible substances used in pharmaceutical formulation. Wetting agents and lubricants such as sodium lauryl sulfate, as well as coloring agents, flavoring agents, excipients, tableting agents, stabilizers, antioxidants, and preservatives, can also be present. It will be appreciated that a pharmaceutical composition can contain multiple different pharmaceutically acceptable carriers.

Pharmaceutically acceptable compositions can include diluents, fillers, salts, buffers, stabilizers, solubilizers and other materials which are well-known in the art. The choice of pharmaceutically acceptable carrier to be used in conjunction with the compounds of the present invention takes into consideration the way the compound is to be administered to the subject. Such preparations may routinely contain one or more salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically acceptable salts thereof in certain embodiments. Such pharmacologically and pharmaceutically acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically acceptable salts can be prepared as alkaline metal or alkaline earth salts, such as sodium, potassium or calcium salts. It will also be understood that a compound can be provided as a pharmaceutically acceptable pro-drug, or an active metabolite can be used.

The pharmaceutical composition may be administered in pharmaceutically acceptable solutions, which may routinely contain pharmaceutically acceptable concentrations of salt, buffering agents, preservatives, compatible carriers, adjuvants, and optionally other therapeutic ingredients.

The pharmaceutical composition may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants. In some aspects the pharmaceutical composition is formulated for administration as a pastille. Examples include those described by U.S. Pat. No. 9,913,873, incorporated herein by reference.

Compositions suitable for oral administration may be presented as discrete units, such as capsules, tablets, lozenges, each containing a predetermined amount of the active agent. Other compositions include suspensions in aqueous liquids or non-aqueous liquids, such as syrups, elixirs and/or emulsions.

In some embodiments, the pharmaceutical composition is administered in combination with one or more therapies. Therapies may be selected from the group consisting of immunotherapy, chemotherapy, radiotherapy, proton therapy, surgery, and combinations thereof. The composition may be administered before, during, or after administration of a therapy. In some aspects, the composition is administered in combination with one or more chemotherapeutic agents. The pharmaceutical compositions described herein may further include one or more chemotherapeutic agents.

The chemotherapeutic agent may be an antineoplastic agent. In some aspects, the antineoplastic agents are selected from the group consisting of antimetabolite agents, antibiotic-type agents, alkylating agents, hormonal agents, immunological agents, interferon-type agents, matrix metalloproteinases, and superoxide dismutase mimics.

Suitable antimetabolite agents may be selected from the group consisting of 5-FU-fibrinogen, acanthfolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrell Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, tyrosine protein kinase inhibitors, Taiho UFT, and uricytin.

Suitable alkylating-type agents may be selected from the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromustine, Tanabe Seiyaku TA-077, tauromustine, temozolomide, teroxirone, tetraplatin, and trimelamol.

Antibiotic-type agents may be selected from the group consisting of Taiho 4181-A, aclarubicin, actinomycin D, actinoplanone, Erbamont ADR-456, aeroplysinin derivative, Ajinomoto AN-201-II, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindamycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024, and zorubicin.

Additional agents may be selected from the group consisting of alpha-carotene, alpha-difluoromethyl-arginine, acitretin, Biotec AD-5, Kyorin AHC-52, alstonine, amonafide, amphethinile, amsacrine, Angiostat, ankinomycin, antineoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, elliprabin, elliptinium acetate, Tsumura EPMTC, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanine derivatives, methylanilinoacridine, Molecular Genetics MGI-136, minactivin, mitonafide, mitoquidone, mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, octreotide, Ono ONO-112, oquizanocine, Akzo Org-10172, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides, Yamanouchi YM-534, and combinations thereof.

The pharmaceutical composition may be administered in combination with a checkpoint inhibitor. In some embodiments a checkpoint inhibitor is selected from the group consisting of a CTLA4 blockade (e.g., ipilimumab), a PD-1 inhibitor (e.g., Nivolumab, Pembrolizumab, and antibody BGB-A317), a PD-L1 inhibitor (e.g., atezolizumab, avelumab, and duralumab), an intrinsic checkpoint blockage (e.g., CISH), and combinations thereof.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or prior publication, or for any other reason. All statements as to the date or representation as to the contents of these documents is based on the information available to the applicants and does not constitute any admission as to the correctness of the dates or contents of these documents.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

EXAMPLES

Between 40,000 to 50,000 patients are diagnosed with head and neck squamous cell carcinoma (HNSCC) each year in the United States. It is the sixth most common cancer worldwide, with an estimated incidence of 500,000 annually. Head and neck cancers include cancers of the oral cavity, oropharynx, hypopharynx, larynx as well as cancers of the nose, paranasal sinuses and salivary glands. Squamous cell carcinomas make up 90% of the head and neck cancers.

Current treatment protocols for advanced head and neck cancer often entail a disfiguring and risky surgical operation. In addition, radiation therapy and chemotherapy used in conjunction with the surgery results in tremendous morbidity for patients with the disease. Despite best efforts, survival rates for late-stage HNSCC remain dismal. It is apparent that a different approach to treatment is needed.

Results of clinical studies suggest that single pathway inhibitors are unlikely to be the answer to control these complex tumors, which have multiple molecular level aberrations. There is increasing acknowledgment among cancer researchers that a multi pathway targeting approach is needed to develop effective treatments and prevent resistance and relapses in order to overcome the current limitations of treatment of HNSCC.

In addition, current immunotherapeutic approaches to treating cancers (e.g., HNSCC), such as the use of checkpoint blockers, has shown unprecedented success in shrinking or halting cancers in some patients. However, these current checkpoint blocker therapies only work in a fraction of patients. Thus, there is a need to increase the effectiveness of these immunotherapeutic approaches so that they may be used alone or in combination with other treatment protocols to treat cancer.

Development of Polypharmaceutical Drug for Treatment of OSCC

It is well-accepted that many diseases such as cancer have a high degree of molecular heterogeneity. Oral squamous cell carcinoma (OSCC) is one such cancer where this molecular heterogeneity poses serious challenges to drug designers who traditionally tend to focus on one or a handful of targets that they seek to inhibit or activate. In reality, multiple biochemical species—proteins that play various functions, genes that code for the proteins and their metabolites—are either part of a network and/or part of a biological process cascade. To compound the situation, these targets often continue to mutate and establish alternative signaling pathways in the tumor when a particular pathway is blocked. Thus, it is vital to have a systems-level understanding to address the evolving dynamics of underlying molecular heterogeneity of the tumor. Therefore, to effectively treat the disease, it is important to not only modulate the obvious targets that are mutated or aberrantly expressed and correlated with the pathogenesis of cancer, but also preserve the housekeeping functions of some of these targets, i.e. to down or upregulate the targets only to the extent necessary towards establishing healthy homeostasis as well as block the alternative signaling pathways that can cause future recurrence of the diseases.

Figure 10:
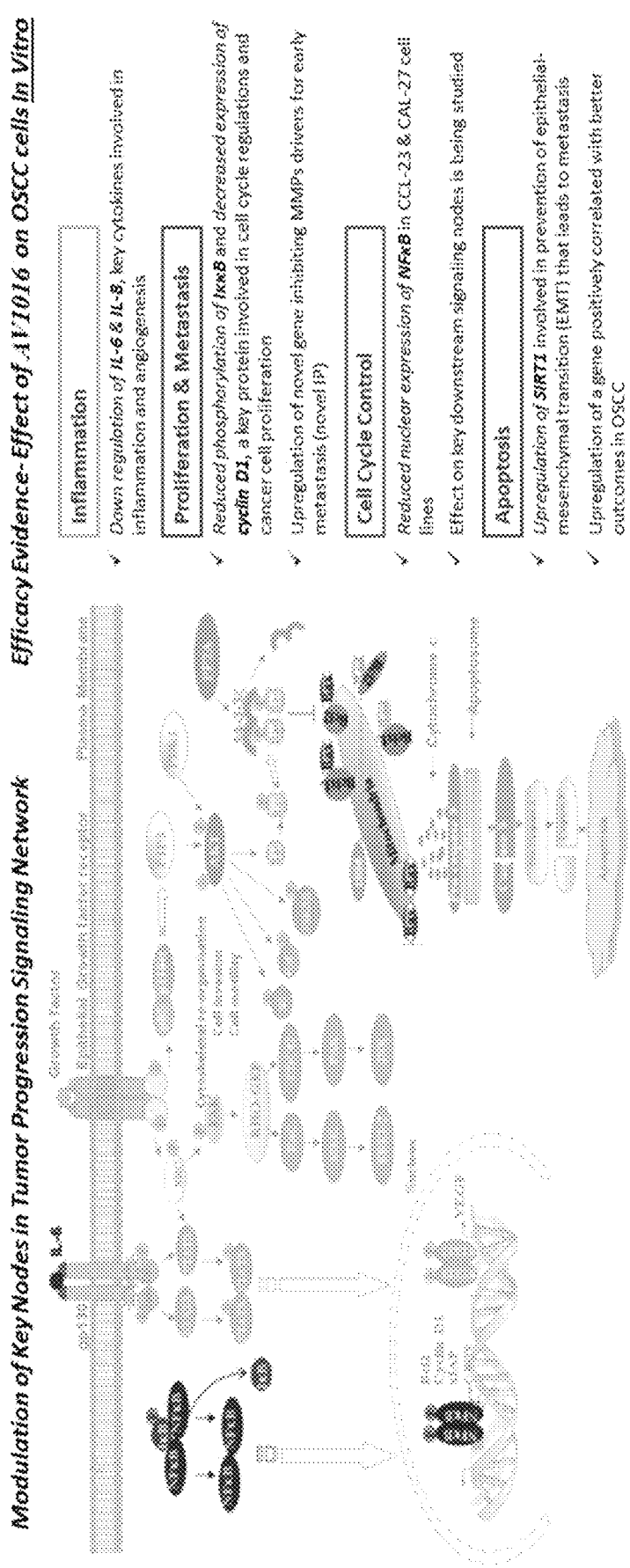
FIG. 10 demonstrates potential mechanisms of action of a composition (AV1016). The modulation of key nodes in the tumor progression signaling networks is shown on the left side of the figure. Early studies indicate a beneficial role for the compositions in improving oral microbiome in addition to managing tumor stem cell growth. Efficacy evidence showing the effect of AV1016 on OSCC cells in vitro is provided on the right side of the figure. Networks affected by AV1016 in OSCC include inflammation, proliferation and metastasis, cell cycle control, and apoptosis.
Figure 11:
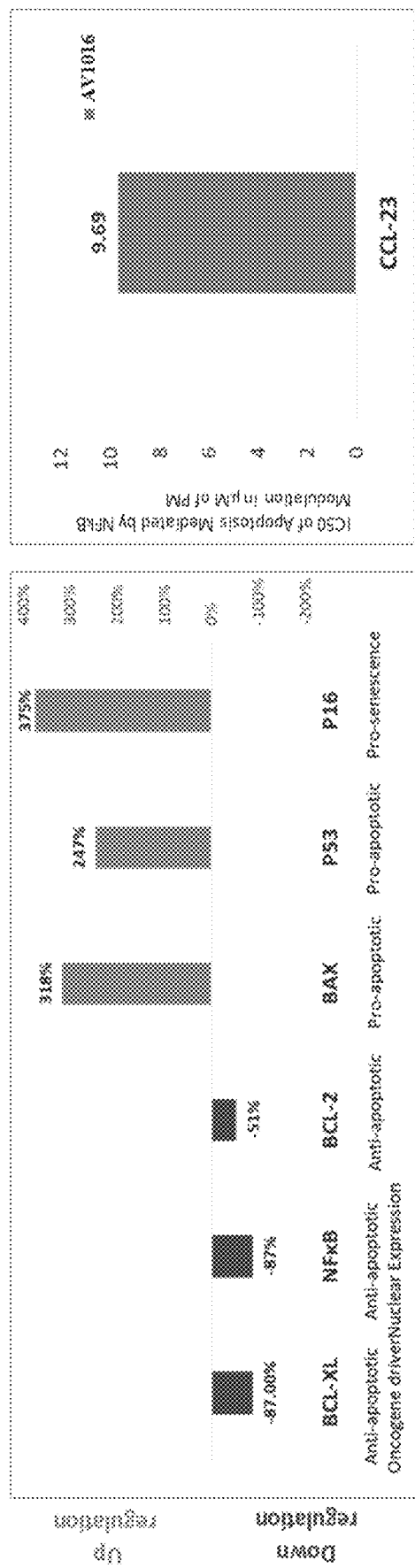
FIG. 11 demonstrates that the composition AV1016 promotes apoptosis and senescence. Relative protein expression levels are shown upon treatment of CCL-23 cells with 30 mg/mL of AV1016 compared to untreated cells using Western blotting. The data in the provided graphs indicate the impact of AV1016 on the key molecular descriptors of OSCC (e.g., p53, NFκB, Bcl2).

A single-agent drug that can effectively address multiple molecular events in a tumor is virtually impossible given that there is enormous diversity of the binding sites of the targets. Therefore, in treatment of many diseases, particularly in case of cancer, it is fairly common to have a cocktail of drugs wherein different drug molecules work through different mechanisms and on different targets, for example, one or more of those targets identified in FIG. 10 and/or in Table 2, below. For example, in certain aspects, the compositions disclosed herein modulate one or more of the targets identified in Table 2. However, one of the most common problems associated with such cocktails is that the number of unique molecules in a cocktail is limited to a handful because interactions among these molecules often lead to unwarranted effects. A second issue is that the molecules in the drug cocktail lack true synergy that can overcome the resistance or recurrence mechanisms and produce a durable clinical response. Thus, there is a need for a polypharmaceutical drug containing multiple molecules that are capable of pleiotropic and truly synergistic action to address vast molecular heterogeneity of the tumor and the tumor microenvironment.

Plant-derived drugs used in traditional systems of medicine are naturally occurring polypharmaceuticals. The bioactive molecules in such drugs, which are usually the metabolites produced by the plants, are the result of millions of years of evolution. Nature has explored chemical-diversity space extensively with a vast array of organic/biological scaffolds and through combinatorial biology and under evolutionary selection pressure has produced a chemical library unmatched by any combinatorial library produced by humans. Furthermore, structural scaffolds on which many related compounds are based have been under intense selection, both for targeting selectivity and high potency for many millions of years.

Plant-derived bioactive molecules generally can be broken down into various classes such as polyphenols, terpenes, alkaloids, sugars, peptides, and large molecules, including proteins and polysaccharides. Many of the molecules have been studied extensively for their medicinal properties. In the case of polyphenols, for example, the following four molecules have been extensively tested for their anti-cancer properties.

Structures of Curcumin, ECGC, Quercetin and Resveratrol

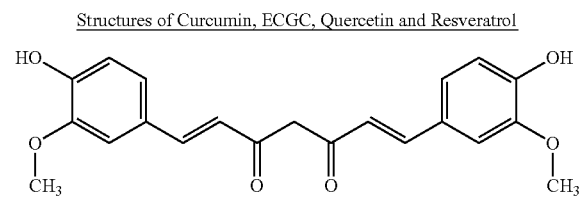

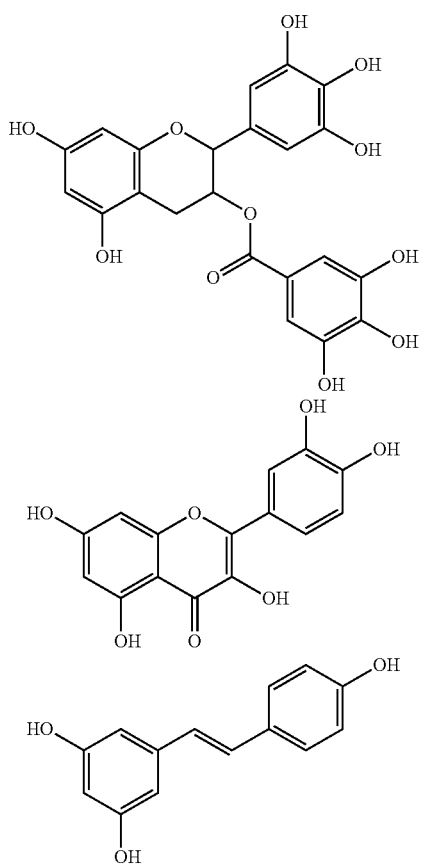

The most well-known example of an anti-cancer drug is Taxol which is a terpenoid.

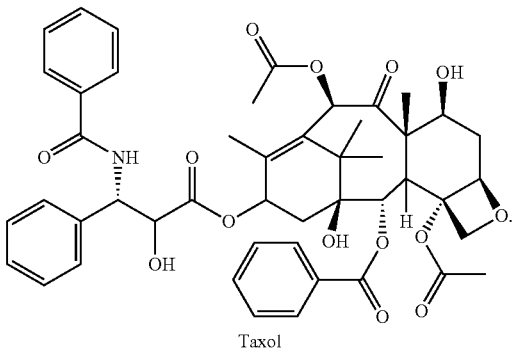 [SMILES: CC(=O)O[C@H]1C(=O)[C@@]2(C)C([C@H](OC(=O)c3ccccc3)[C@]3(O)CC(OC(=O)C(O)[C@@H](NC(=O)c4ccccc4)c4ccccc4)C(C)=C1C3(C)C)[C@]1(OC(C)=O)CO[C@@H]1C[C@@H]2O]

Taxol

While these molecules have shown excellent efficacy for many diseases, they represent reductionist thinking for creating drugs from the botanical sources (see, FIG. 1). However, such a reductionist approach fundamentally fails to leverage the evolutionary advantages of a natural, combination therapeutic. The evolutionary purpose behind the creation of a large diversity of molecules, while producing structurally similar molecules within a single class, is that functional superiority is achieved not by a single molecule, but rather a combination of the molecules. Different molecules play different roles, including increasing pharmacodynamic effect by binding to common or multiple targets in a network, creating redundancy in cases of target mutation, assisting the transport of pharmacodynamic molecules, and improving overall absorption, distribution, metabolism, and excretion (ADME), to name a few. This principle of evolutionary biology—multiple molecules exerting their effect as a part of a system or a consortium of bioactive compounds versus a single, silver-bullet agent—is the basis of designing a polypharmaceutical drug.

Figure 2:
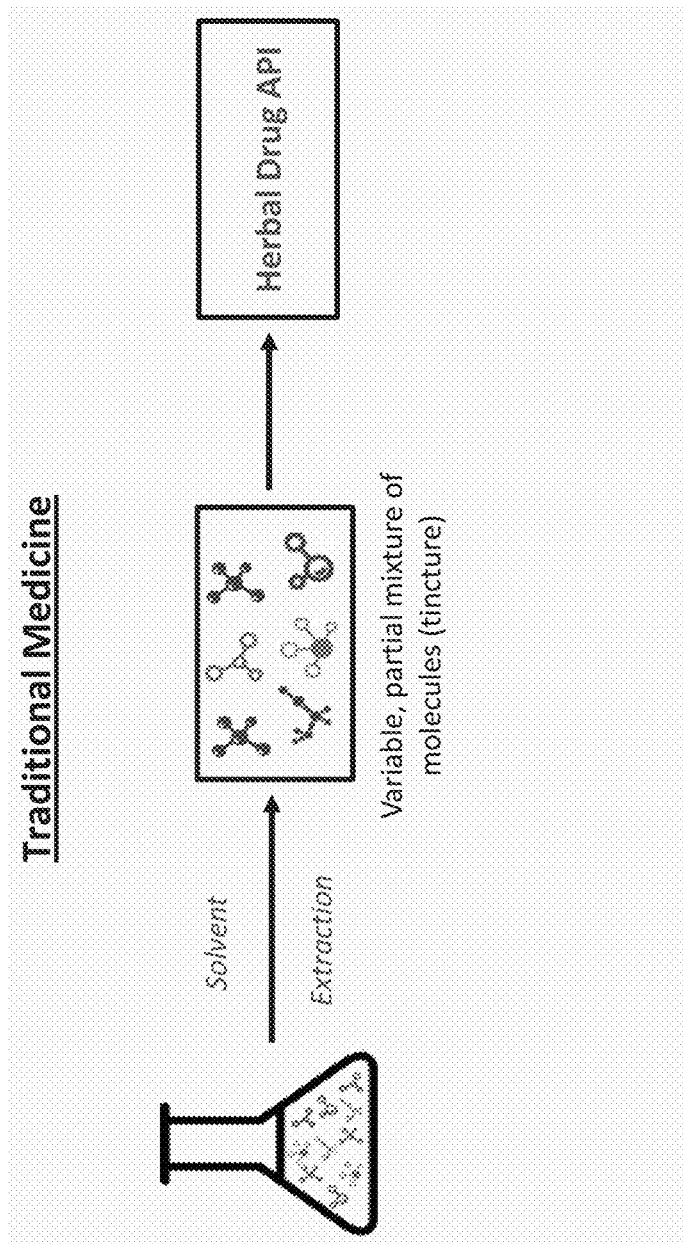
FIG. 2 depicts a schematic of a second process for developing a drug from a plant source. The schematic demonstrates the use of solvent extraction to obtain a variable mixture of molecules from a plant source and the use of that mixture to form an herbal drug active pharmaceutical ingredient (API) (e.g., a simple extract or tincture-based drug). The resultant drug will consist of multiple molecules, but the relative ratios of the molecules will be dependent on and limited by the extraction process used.

A traditional approach for designing a polypharmaceutical drug is the use of a "crude" plant extract as shown in FIG. 2. While such a therapeutic drug consists of multiple molecules, the composition of the extracts, as well as the relative ratios, are dependent on and limited by the extraction process used. Such a composition is not optimized for a disease of interest and often lacks sufficient potency.

In a plant, the gene clusters responsible for production of different classes of metabolites generally tend to code for a biosynthetic pathway that produces the molecules belonging to the same class bearing structural similarity. These "co-evolved" molecules are intended to work together functionally. Additionally, different classes of molecules further tend to synergize where each class of molecule is designed to play a distinct role ranging from its versatility in binding to the proteins of interest, to avoidance of the toxicity, to enabling the absorption of the pharmacologically active molecules. While a botanical source produces these compounds in a range of ratios relative to each other, the naturally occurring ratios is not optimized for a human disease of interest, particularly so for a molecularly heterogeneous cancer such as OSCC. Therefore, while a selection of plant(s) with the right classes of pharmacologically active molecules is an important first step in developing a botanical drug, optimizing ratios of different bioactive compounds in the context of the disease biology is vital. Therefore, alteration in natural ratios of the classes of compounds that occur in nature is proposed so as to create new drug where the levels of the compounds are optimized for a given disease of interest.

Figure 3:
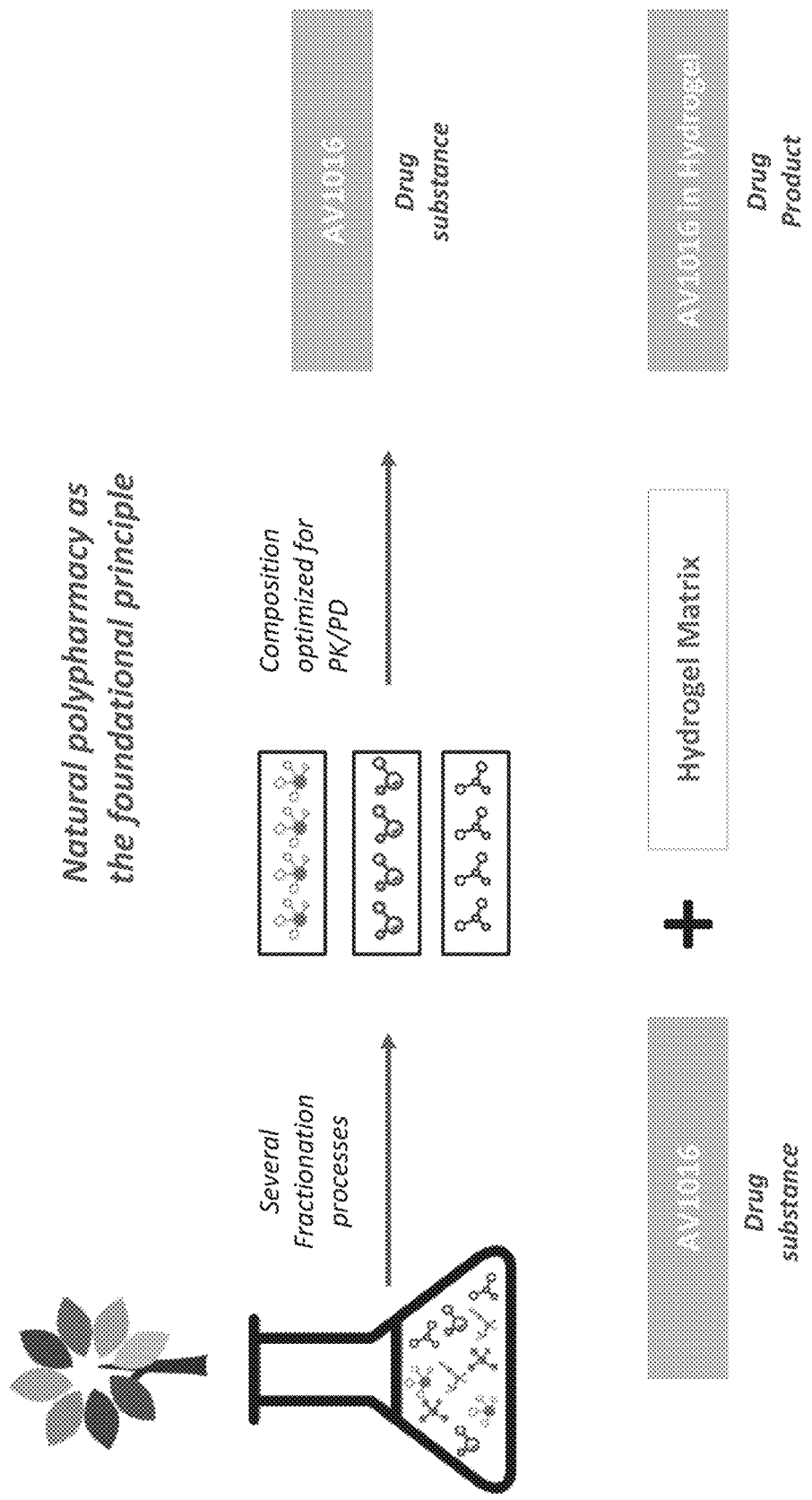
FIG. 3 illustrates a schematic of a third process for developing a drug from a plant source. The schematic demonstrates fractionation processes to create rich fractions of the molecules present based on their physicochemical properties. The biological activities of the rich extracts are tested separately and in combination for the phenotypic response that is relevant for the disease of interest as well as the modulation of genes and proteins whose functions are believed to impact the diseases. Based on these results, the ratios of different extracts rich in different classes of molecules are adjusted in relation to each other to achieve the optimum pharmacological effect for a pharmaceutical drug substance (e.g., relationally designed botanical drug). For example, to make the composition AV1016, a high polarity extract, a medium polarity extract and a low polarity extract were combined in a 3:6:1 ratio by weight, respectively, using mechanical blending process. In another example, to make the composition AV2017, a high polarity extract, a medium polarity extract and a low polarity extract were combined in a 1:1:1 ratio by weight, respectively, using mechanical blending process.
Figure 4:
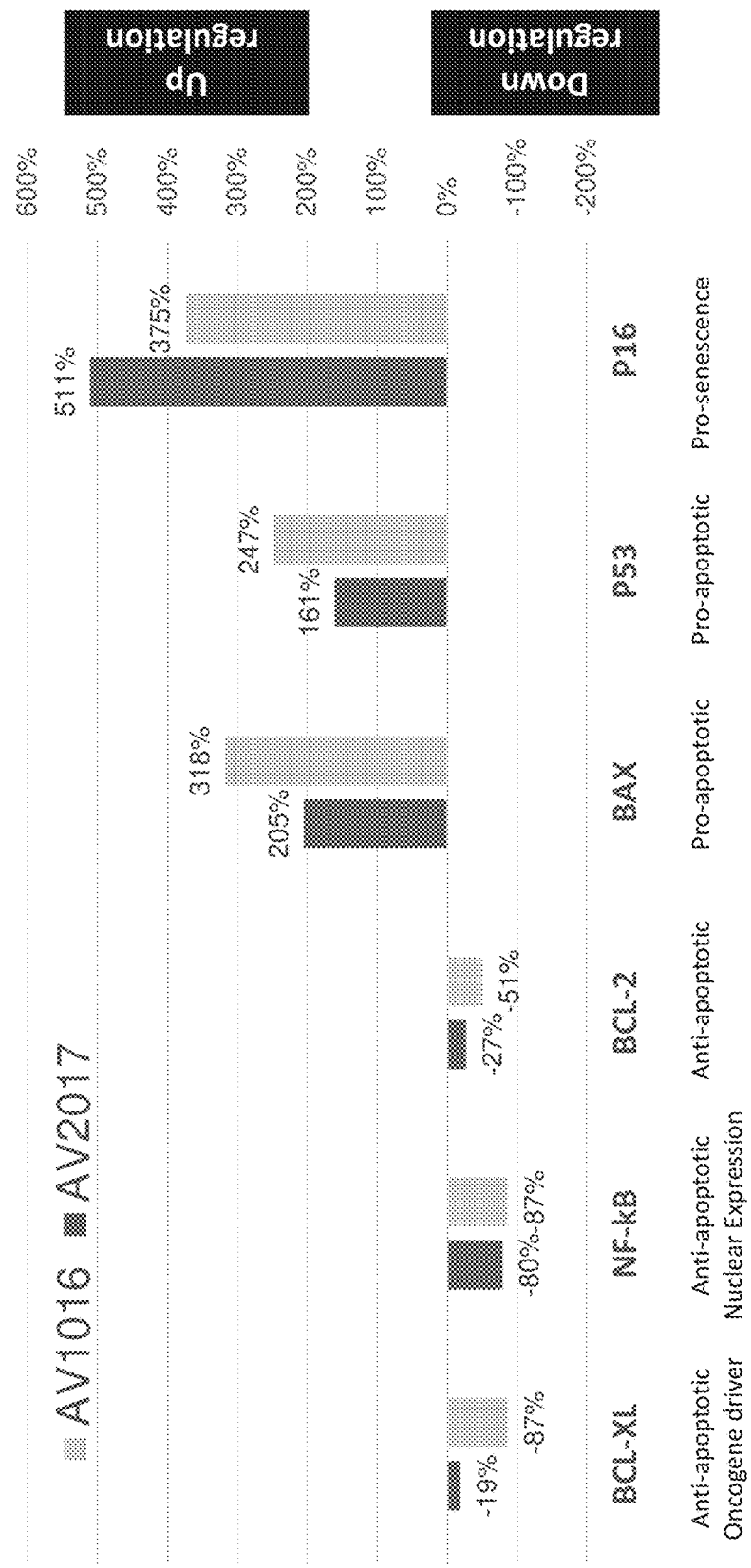
FIG. 4 depicts a graph of varying levels of relative protein expressions observed in CCL-23 cells when exposed to two different ratios of High Polarity, Medium Polarity, and Low Polarity extracts of *Curcuma longa*.
Figure 5:
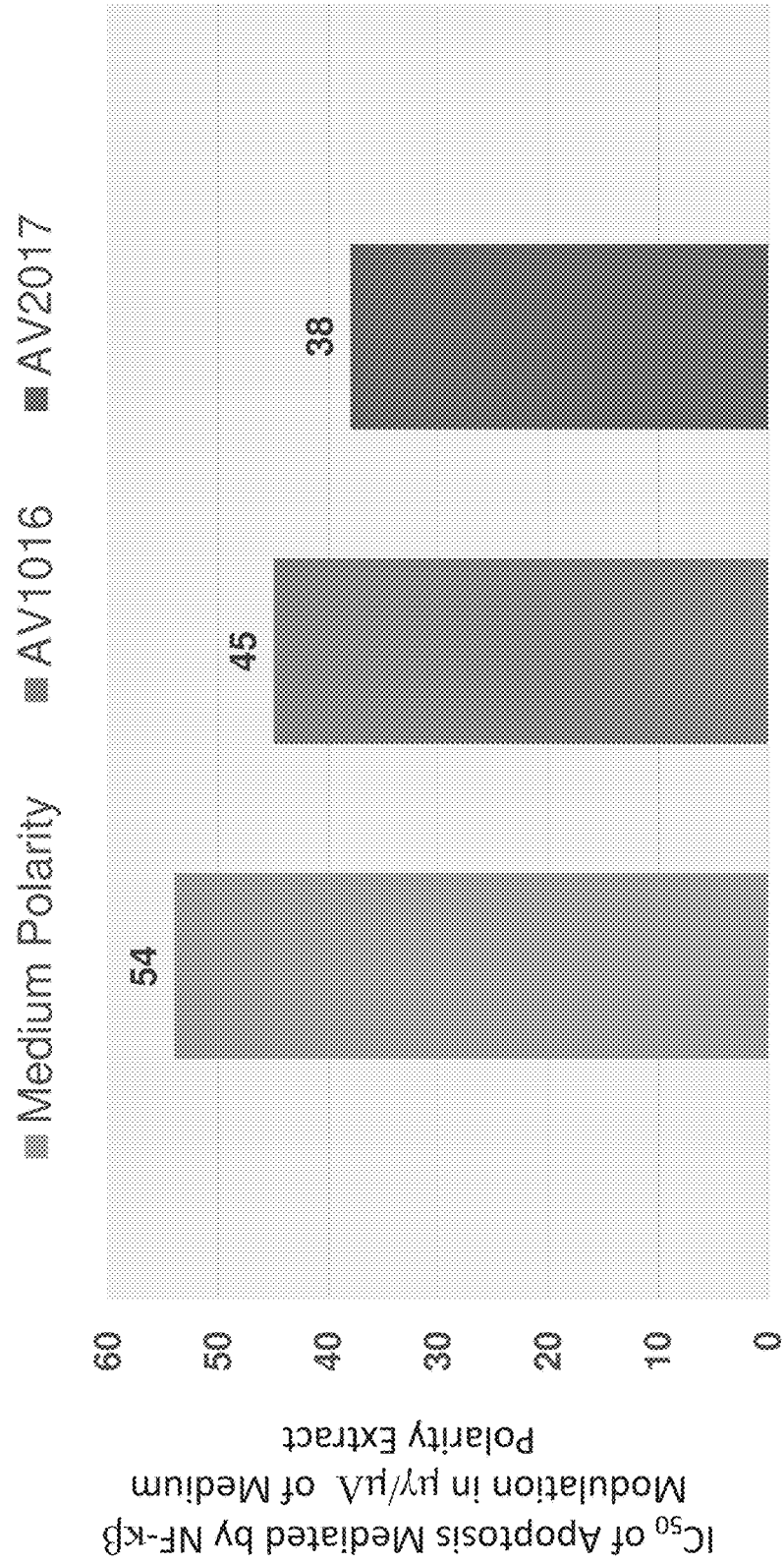
FIG. 5 provides a graph of CCL-23 cell killing potency of three different ratios of High Polarity, Medium Polarity, Low Polarity extracts. The number above each bar graph indicates the concentration of curcumin that results in similar observed 50% death of CCL-23 cells ($IC_{50}$) in all three samples tested.
Figure 6:
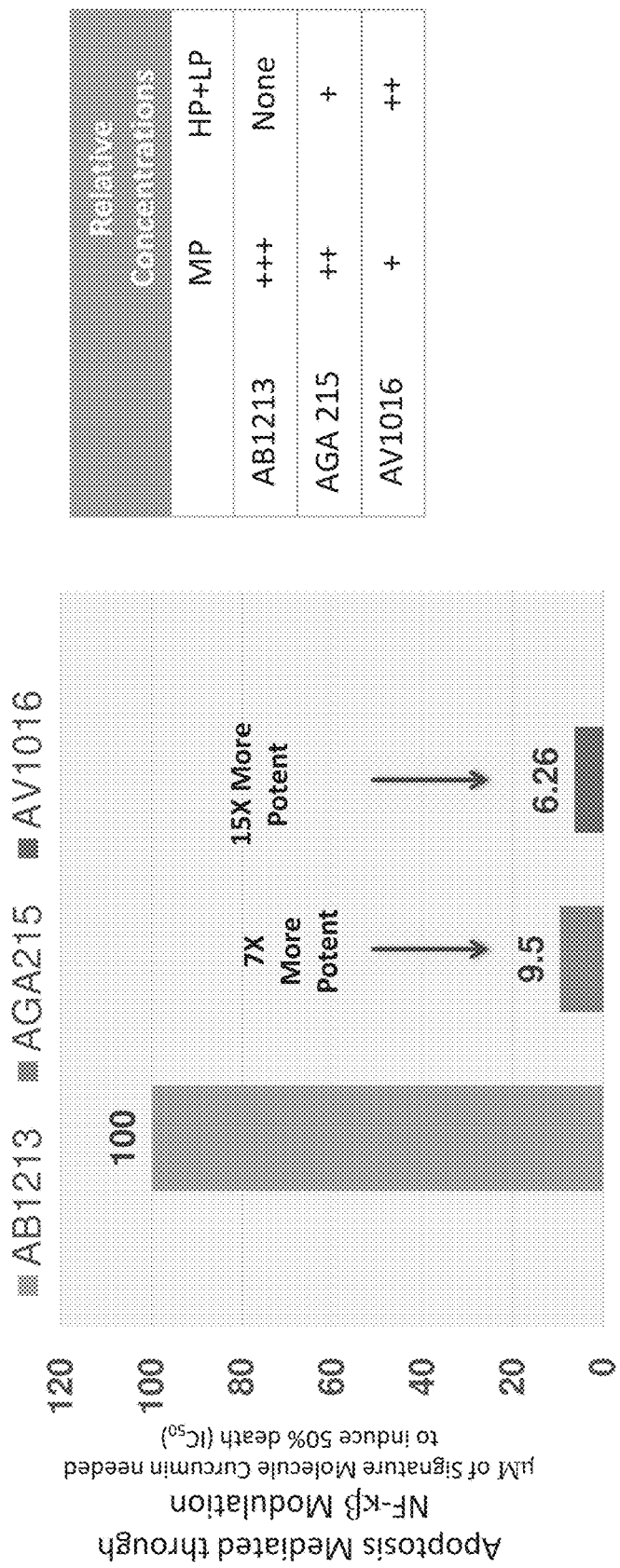
FIG. 6 provides a graph of apoptosis achieved through NF-kb modulation of three different formulations of High (HP), Medium (MP), and Low (LP) polarity extracts. The numbers above the bars are the concentration of curcumin present in each formulation. The compositions identified as AGA215 and AV1016 require less curcumin to achieve the same degree (50%) of cell death. The panel on the right shows the relative amounts of HP, MP, and LP in each of the formulations tested. The graph shows that the same level of phenotypic effect (cell death) can be achieved by reducing the levels of a particular polyphenol and it is believed that other polyphenols present in medium polarity extract contribute to apoptosis mediated cell death. By going from a single molecule-based approach to a multiple molecule-based approach the effective concentration of the therapeutic agents can be reduced and thus the therapeutic index can be widened.
Figure 7:
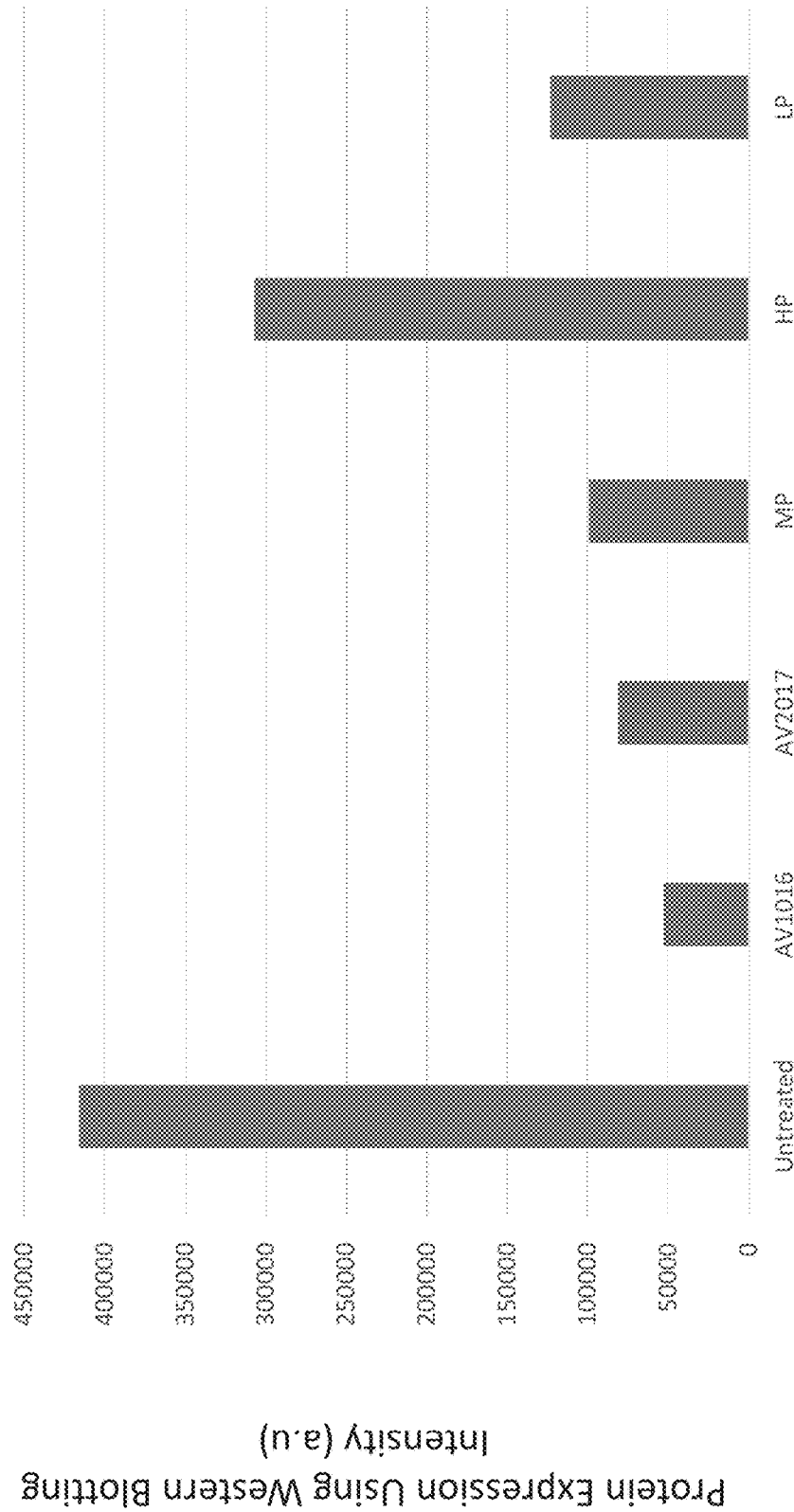
FIG. 7 depicts a graph that shows that relative to the individual extracts rich in Medium Polarity (MP), High Polarity (HP) and Low Polarity (LP) Compounds, two combinations of extracts—AV1016 and AV2017—show higher down-regulation indicating synergistic pharmacological response.
Figure 8:
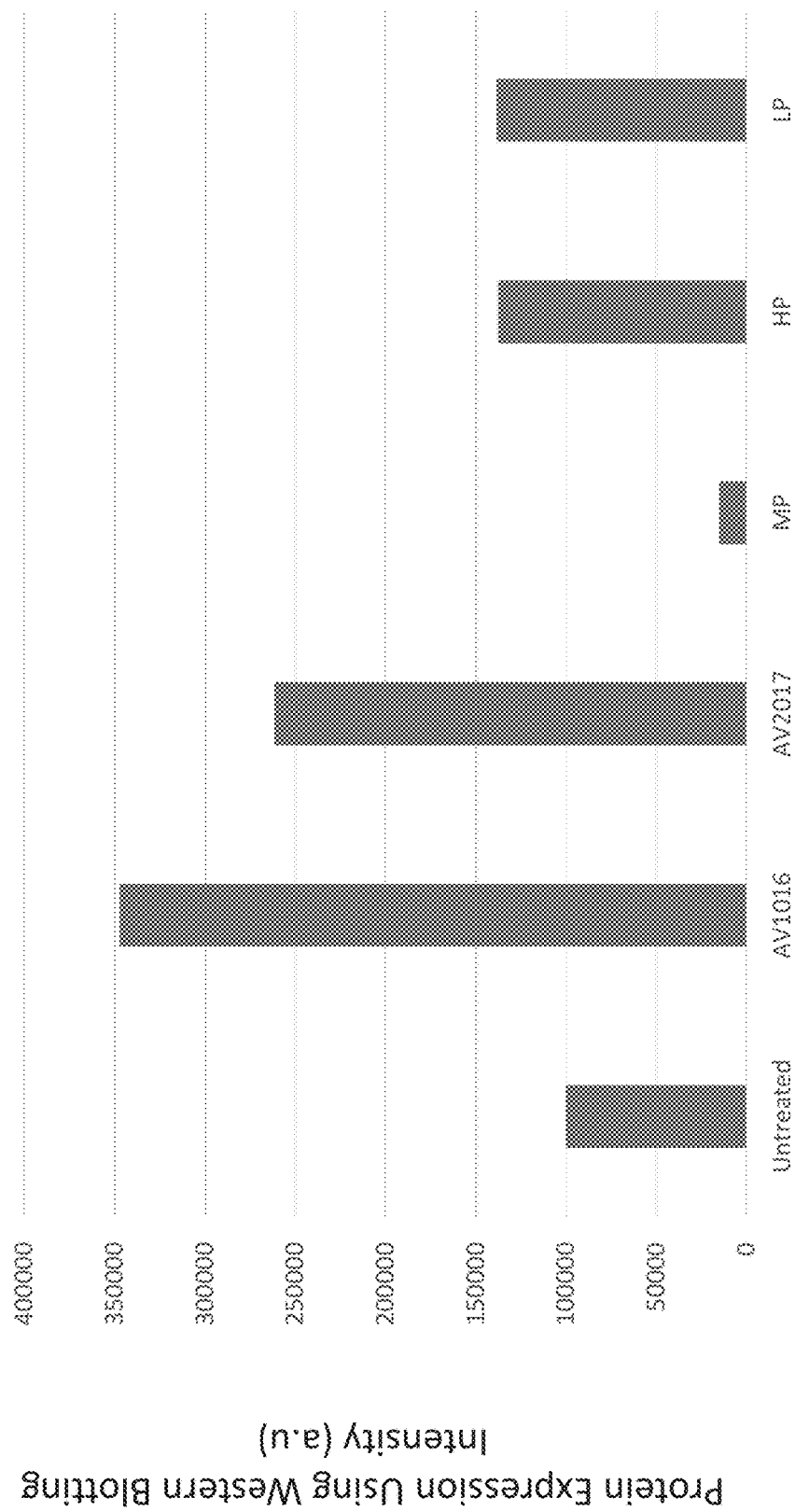
FIG. 8 represents a graph that demonstrates that, compared to individual extracts rich in Medium Polarity (MP), High Polarity (HP) and Low Polarity (LP) compounds, two combinations of extracts—AV1016 and AV2017—show higher upregulation indicating synergistic pharmacological response.
Figure 9:
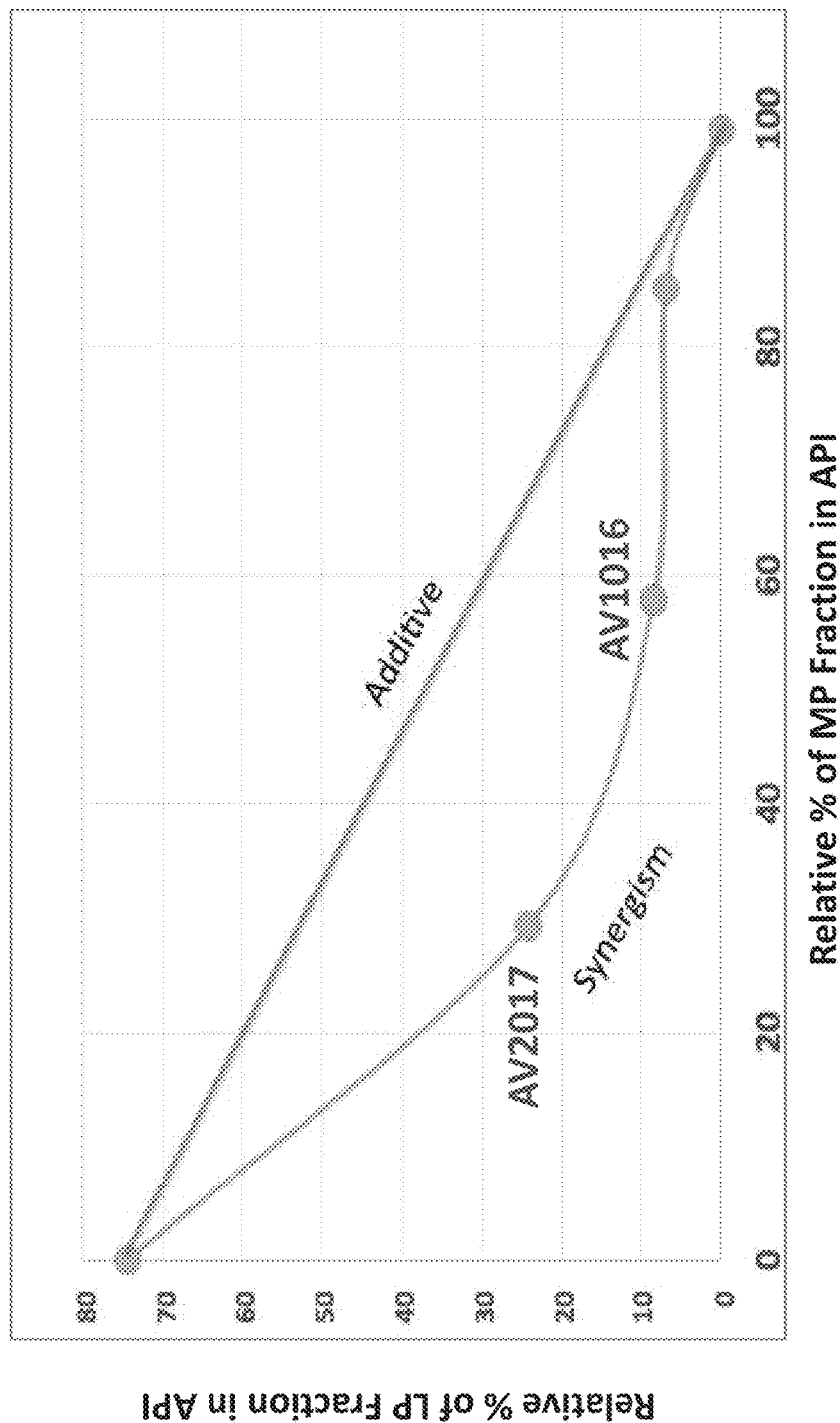
FIG. 9 provides a graph showing an isobologram indicating strong synergy between medium polarity (MP) and low polarity (LP) extracts. Each data point represents $IC_{50}$ of an MP+LP combination that yields equivalent NF-KB mediated apoptosis in vitro. The zone above the Additive line indicates antagonism and the zone below the Additive line indicates synergy. The combinations of extracts AV1016 and AV2017 are in the synergistic region of the isobologram.

In addition to size, conformational flexibility of the molecular backbone, and functional groups that are important in terms of the transport of the molecules and ability to bind to targets, another aspect that determines the physico-chemical properties of the molecules and their ability to act as a drug is relative polarity of the molecules. As shown in FIG. 3, the present inventors fractionated the molecules present in a botanical source using the processes that create rich fractions based on their physico-chemical properties. The present inventors then tested the biological activity of the rich fractions separately and in combination to optimize the relative ratios of the active compounds.

Curcuma longa Based Botanical Polypharmaceutical Drug

Based on the foregoing principles, the inventive subject matter comprises the development of a polypharmaceutical drug that primarily uses fractions comprising rich extracts of Curcuma longa, a perennial herb grown in many parts of the world, but in a unique ratio (i.e., different than that found in nature) optimized for treating human diseases. C. longa and more particularly, curcumin, one polyphenolic metabolite from C. longa, is extensively studied for its medicinal properties. While curcumin is often used as a proxy for overall pharmacological properties of C. longa, it is only one of over 200 small bioactive molecules found in C. longa. In keeping with the principles outlined above, and with the objective of creating a polypharmaceutical composition where multiple molecules act synergistically to provide superior pharmacological response, an inventive composition is developed where major classes of molecules from C. longa are combined to create polypharmaceutical compositions.

The polypharmaceutical compositions comprise a combination of extracts containing low or non-polar compounds, medium polarity compounds, and highly polar compounds in a variety of ratios.

A low or non-polar extract of C. longa is created by extracting the dried, powdered rhizome with a solvent system that has a dielectric constant less than 5 or a relative polarity of less than 0.2. This extract is rich in a class of compounds known as terpenoids and its concentration is no less than 50% by weight. The extract is usually characterized by the presence and levels of a signature compound Ar-Turmerone.

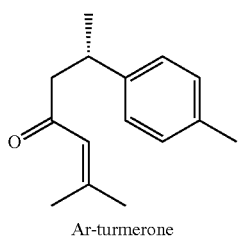 [SMILES: CC(C)=CC(=O)C[C@H](C)c1ccc(C)cc1]

Ar-turmerone

An extract rich in medium polarity molecules is obtained by extracting C. longa using a solvent system that has a dielectric constant between 5 and 25 or a relative polarity is equal to or between 0.25 and 0.6. Such an extract is generally rich in a class of compounds known as polyphenols whose concentration ranges from at least 90% curcuminoid and is usually characterized by a signature compound Curcumin. Other examples of polyphenols are described by Li et al., Chemical Composition and Product Quality Control of Turmeric (Curcuma longa L.), Pharmaceutical Crops, 2011, 2:28-54, the entire contents of which incorporated herein by reference.

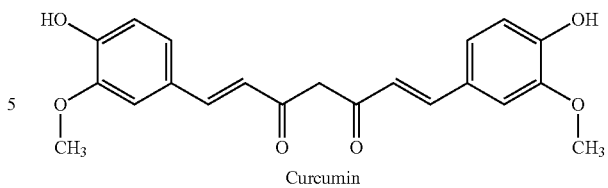

Curcumin

An extract rich in high polarity molecules is obtained by extracting C. longa using a solvent system that has a dielectric constant greater than 25 or a relative polarity greater than 0.6. Such an extract is usually rich in nitrogen-containing compounds and polysaccharides whose concentration ranges from 2.5%-15% and at least 25% respectively.

The values for relative polarity are normalized from measurements of solvent shifts of absorption spectra and are described in Christian Reichardt, Solvents and Solvent Effects in Organic Chemistry, Wiley-VCH Publishers, 3rd ed., 2003, the contents of which are incorporated by reference herein.

Table 1 below summarizes the ratios of the yields of the extracts obtained relative to the weight of the processed starting materials. Approximately only 5% of the desired components are obtained for each type of extract from the raw plant material used.

TABLE 1

Summary of Extracts Obtained Using Various Fractionation Processes

| Extract | Ratio of Extracted Product Obtained: Plant material used | Signature Molecules |
| --- | --- | --- |
| High Polarity | ~1:15 | Polysaccharides, Nitrogen containing compounds |
| Medium Polarity | ~1:25 | Curcuminoids |
| Low Polarity | ~1:14 | Turmerones |

An exemplary composition, referred to herein as AV1016, was made by combining a high polarity extract, a medium polarity extract and a low polarity extract in a 3:6:1 ratio by weight, respectively, using mechanical blending process. Another exemplary composition, referred to herein as AV2017, was made by combining a high polarity extract, a medium polarity extract and a low polarity extract in a 1:1:1 ratio by weight, respectively, using mechanical blending process.

Several studies have documented constituent activation of NF-kB in head and neck cancer cell lines. Therefore, it is hypothesized that the inhibition of NF-kB could play an important role in the control of cancer development. Consequently, compositions of varying amounts of different rich extracts were tested for their ability to cause apoptosis of cancer cells in oral cancer cell lines.

The mechanism of growth suppressive effect of compositions of different ratios of low polarity (LP), medium polarity (MP) and high polarity (HP) extracts was elucidated by measuring the expression of cell cycle, apoptotic and autophagic genes. Protein extracts prepared from cells treated with the fixed, cell-death inducing concentrations of different formulations for the time periods ranging from 2 to 6 hours were analyzed by the gel shift assay to determine the level of NF-kB, P53, P16 and related genes. Protein extracts were also prepared from untreated cells and cells treated with 0.05% DMSO (the amount present in preparations), as controls. The analysis showed a reduction in the level of NF-kB, upregulation in P53 and P16 within 4 hours of treatment followed by a dramatic decrease in NF-kB after 6 hours.

Phenotypic changes induced by the specific compositions clearly indicate a specific targeting of a definitive gene pathway for cell killing (apoptosis and autophagic signaling axis). The effect of HP, MP, and LP clearly signaled differences in effect on certain genes, with demonstration of synergistic targeting on multiple gene pathways, when combined in some definite proportions.

Methods of Treatment Using *Curcuma longa* Based Botanical Polypharmaceutical Drug Head and Neck Squamous Cell Carcinoma's (HNSCC) and its subset, Oral squamous cell cancer (OSCC) arise through a series of molecular mutations that lead to uncontrolled cellular growth from hyperplasia to dysplasia to carcinoma in situ followed by invasive carcinoma. Major risk factors include tobacco and alcohol consumption along with environmental and genetic factors (Brinkman and Wong, Curr Opin Oncol. 18(3):228-33, 2006; Figuerido et al., Drug Discovery Today Disease Mechanisms 1(2):273-281, November 2004). These cancers are usually detected at late-stages when the disease has advanced and therefore results in poor prognosis and survival.

Currently, surgery and radiotherapy are the primary treatments, but due to the location in the head and neck this usually results in postoperative defects and functional impairments in patients. Therefore, early disease detection is imperative because it can result in a more effective treatment with superior results.

Recently, initiatives such as Cancer Genome Atlas (TCGA) have mapped the genome wide effect of individual genes on tumor growth. This provides a framework for unraveling the genomic, transcriptomic, proteomic and metabolomics profile for HNSCC and OSCC.

The emerging picture reveals significant heterogeneity, which presents challenges for targeted drug treatment, but also opportunities for creating polypharmaceutical compositions to target this heterogeneity.

The present inventors are studying the effect of AV1016 on wide ranging genomic, transcriptomic, proteomic, and metabolomics markers, including, but not limited to those listed in Table 2, below. Accordingly, in certain aspects, the compositions disclosed herein modulate or otherwise affect one or more of the pathways listed in Table 2. In certain embodiments, the compositions disclosed herein modulate the expression (e.g., increase or decrease the expression) of one or more of the biomarkers listed in Table 2.

TABLE 2

Potential Pathways Impacted by AV1016 and Examples of Reporter Molecules and Biomarkers for Assessing Impact

| Pathways and Factors | Example Reporter Biomarkers |
|---|---|
| Chemokine receptors | CXCR2 |
| | CXCR4 |
| | CCR7 |
| Viral | HPV, EBV |
| Methylation markers | |
| Metalloproteinases | MMP-1, MMP-2, MMP-3, MMP-8, MMP-9, MMP-10 |
| Interleukins | IL-6, IL-8 |
| | IL-1, IL-1Beta, |
| MicroRNA's | miR-106b-25 cluster, miR-375, miR451, miR-125a, miE-200a, miR-205, miR-138, |

TABLE 2-continued

Potential Pathways Impacted by AV1016 and Examples of Reporter Molecules and Biomarkers for Assessing Impact

| Pathways and Factors | Example Reporter Biomarkers |
|---|---|
| Melanoma Associated Genes | MAGE |
| Centrosome abnormalities | |
| Cytokeratins | |
| Oncogenes and Tumor suppressor genes | TP53, NOTCH1, CDKN2A |
| Genes implicated in cell cycle | CDKN2A, RB1, CDK12, CDKN1B, CCND1, CDKN1A, CDKN2C, Ki67/MIB-1, AgNORs, Cyclin D1, VRK1, EGFR, EGFR variants, K-RAS, NF-KB, AURKA/STK15/BTAK, ERCC1, XRCC1 |
| Angiogenic factors | VEGF, HIF-1 |
| Structural related markers | EMT, b-Tubulin, CD 44, CD 68 |
| Epigenetic modifiers | Aberrant DNA methylation, Histone modifications and miRNAs |
| Transcription Factors/regulators | VHL, NFKB, GATA3, TSHZ3, EP300, CTCF, TAF1, TSHZ2, RUNX1, MECOM, TBX3, SIN3A, WT1, EIF4A2, FOXA1, PHF6, CBFB, SOX9, ELF3, VEZF1, CEBPA, FOXA2 |
| Histone Modifier | MLL3, MLL2, ARID1A, PBRM1, SETD2, NSD1, SETBP1, KDM5C, KDM6A, MLL4, ARID5B, ASXL1, EZH2 |
| Genome Integrity | TP53, ATM, ATRX, BRCA2, ATR, STAG2, BAP1, BRCA1, SMC1A, SMC3, CHEK2, RAD21, ERCC2 |
| MAPK signaling | KRAS, NF1, MAP3K1, BRAF, NRAS, MAP2K4, MAPK81P1 |
| PI(3)K signaling | PIK3CA, PTEN, PIK3R1, TLR4, PIK3CG, AKT1 |
| TGF-Beta signaling | SMAD4, TGFBR2, ACVR1B, SMAD2, ACVR2A |
| Wnt/Beta-catenin signaling | APC, CTNNB1, AXIN2, TBL1XR1, SOX17, |
| Histone | HIST1HIC, H3F3C, HIST1H2BD |
| Proteolysis | FBXW7, KEAP1, SPOP |
| Splicing | SF3B1, U2AF1, PCBP1, |
| HIPPO signaling | CDH1, AJUBA |
| DNA methylation | DNMT3A, TET2 |
| Metabolism/Metabolites | IDH1, IDH2, Intercept, Alanine, Choline, Leucine + Isoleucine, Glutamic Acid, 120,0801 m/z, PhenylAlanine, alpha-Aminobutyric acid, Serine, Trimethylymine, Piperidine |
| NFE2L | NFE2L2, NFE2L3 |
| Protein phosphatase | PPP2R1A, PTPN11 |
| Ribosome | RPL22, RPL5 |
| TOR signaling | MTORSTK11 |
| Other | TNF-A, NFKB, Bmi-1, P16, NAV3, LRRK2, MALAT1, ARHGAP35, POLQ, NCOR1, USP9X, NPM1, HGF, EPPK1, AR, LIFR, PRX, CRIPAK, EGR3, B4GALT3, MIR142, GAN, TIMP4, BCL-XL, BCL-2, BAX, CA9, TP53BP2, HOXB9, NFKB1A |

Use of *Curcuma longa* Based Botanical Polypharmaceutical Drug to Prime Tumors

Currently available cancer therapies generally involve multiple treatment modalities, which may include immunotherapeutics. Immunotherapy drugs belonging to a group called checkpoint inhibitors are antibody-based agents that mobilize the immune T-cell response. Checkpoint mechanisms, such as those based on PD-1 and PD-L1, are the body's normal mechanisms to prevent T cells from attacking healthy tissues. However, cancer cells are able to hijack this mechanism by sending false signals to the body's T cells, thereby masquerading cancer cells as normal, non-cancerous cells. The immune system responds by turning the T cell and other macrophages off, allowing cancer cells to multiply. Checkpoint inhibitors, by various mechanisms, make these cancer cells recognizable and thus, allow the immune system (e.g., T cells), to activate and thus destroy cancer cells.

However, checkpoint inhibitors are not necessarily effective for all patients. One reason checkpoint inhibitors may be ineffective is that cancerous tumor may have a limited number of T cells to be turned on. Tumors may be termed "hot" when they are filled with T cells and "cold" when they contain only a few T cells. The classifying of a tumor as "cold" or "hot" can be referred to as an immunoscore. "Hot" tumors are generally more sensitive to immunotherapy due to the increased amount of T cells, and therefore patients with "hot" tumors tend to respond to immunotherapy, such as that based on checkpoint inhibitors, better than patients with "cold" tumors.

Figure 12:
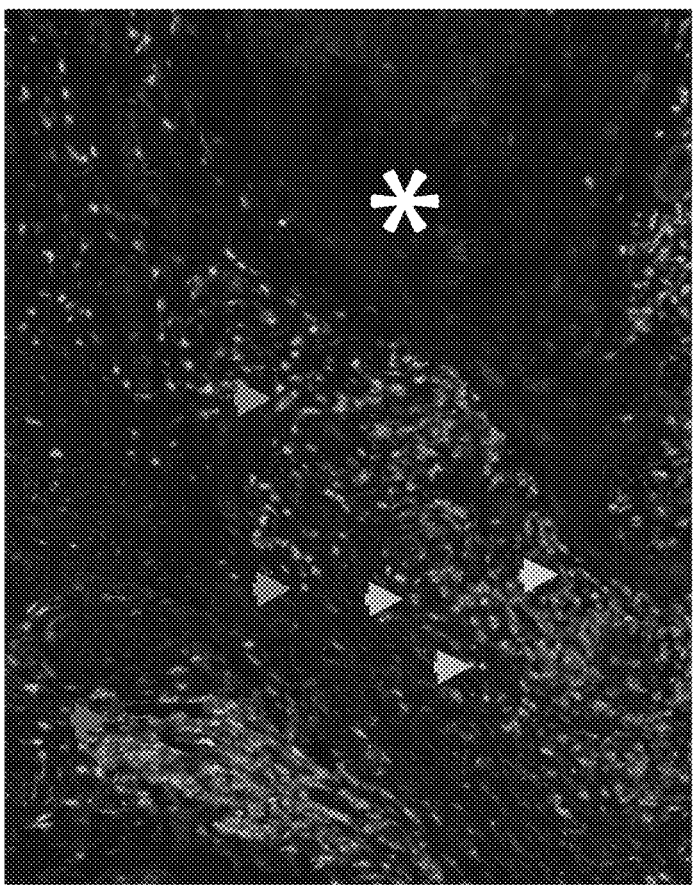
FIG. 12 shows an immunofluorescence (IF) analysis of biopsy samples taken from a patient pre- and post-treatment with AV1016. The pre-AV1016 IF slide (left panel) shows scattered CD8 positive cells on the pre-AV1016 tumor biopsy. The post-AV1016 tumor biopsy (right panel) showed markedly increased CD8 and CD4 T cells and many of these cells are PD-1 positive. There is also PD-L1 expression on tumor cells (red) which was not present on the pre-AV1016 biopsy. This indicates that PD-L1 was expressed in response to T cell infiltration into the tumor microenvironment. This may indicate adaptive PD-L1 expression, which further suggests that an immune checkpoint blockade (anti-PD-1 or anti-PD-L1 antibody) may work on this patient after the patient's tumor has been primed by AV1016. AV1016 (600 mg total dose) was delivered to the oral cavity of Patient A using a hydrogel carrier.
Figure 12:
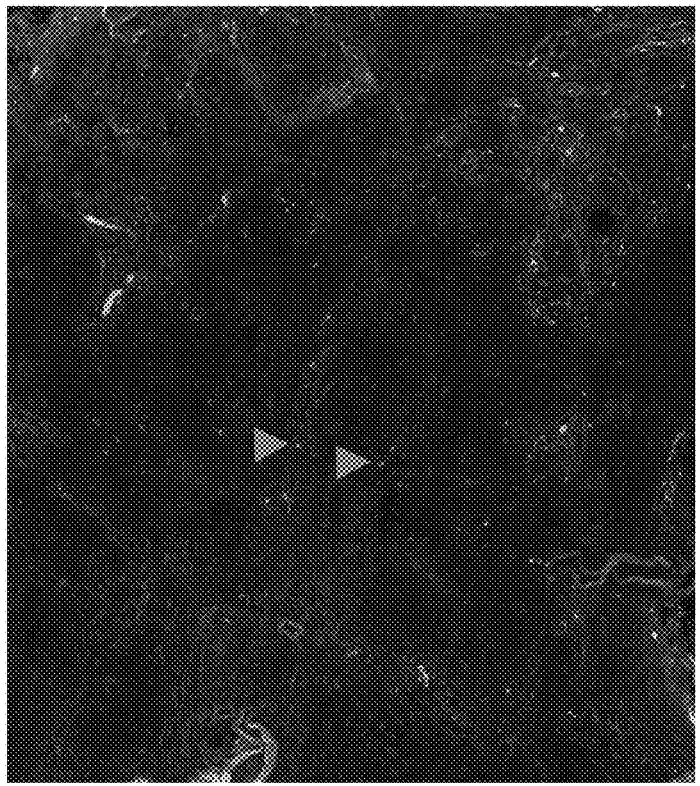

One way to address this issue is to make cold tumors "hot," or in other words to prime the tumor. Priming the tumor may result in an increase in the number of T cells present within the tumor. Surprisingly it has been found that AV1016 acts as a primer of tumors. For example, administration of AV1016 to a patient resulted in a tumor changing from "cold" to "hot," as illustrated in FIG. 12. The patient, a 64-year old male with a history of smoking, had a biopsy tissue sample removed from a tumor in the floor of his mouth (pre-AV1016 administration). The patient then returned to the clinic approximately two weeks later for a scheduled surgical procedure. However, prior to the surgical procedure, the patient was administered AV1016 (600 mg dose) delivered in a hydrogel carrier to the oral cavity of the patient. Approximately 24 hours after receiving AV1016, the patient underwent surgical resection of his tumor (post-AV1016 administration). The pre- and post-AV1016 immunofluorescence results illustrated in FIG. 12 evidence that the patient's tumor changed from "cold" to "hot" after administration of AV1016. Thus, AV1016 demonstrated efficacy as a primer of tumors for use in combination with other immunotherapies.

What is claimed is:

1. A method of increasing T-cell infiltration in a tumor of a subject, such method comprising a step of administering a pharmaceutical composition to the subject, wherein the composition comprises:
   (a) one or more high polarity compounds isolated from *Curcuma longa* using a high polarity solvent system having a dielectric constant of greater than about 25 and a relative polarity value of greater than about 0.6 and selected from the group consisting of proteins, polysaccharides, and peptides;
   (b) one or more medium polarity compounds isolated from *Curcuma longa* using a medium polarity solvent system having a dielectric constant of about 5 to about 25 and a relative polarity value of about 0.25 to about 0.6 and selected from the group consisting of polyphenols, curcumin, demethoxycurcumin, and bisdemethoxycurcumin; and
   (c) one or more non-polar compounds isolated from *Curcuma longa* using a non-polar solvent system having a dielectric constant of less than about 5 and a relative polarity value of less than about 0.2 and selected from the group consisting of terpenoids, ar-turmerone, α-turmerone, and β-turmerone;
   wherein the tumor is oral squamous cell carcinoma.

2. The method of claim 1, wherein one or more of the high polarity compounds, medium polarity compounds and non-polar compounds are micronized.

3. The method of claim 1, wherein the composition comprises about 11-15% w/w of the high polarity polysaccharides, about 41-44% w/w of the medium polarity compound curcumin, and about 3-4% w/w of the non-polar compound ar-tumerone.

4. The method of claim 1, wherein the composition comprises a [3]:[6]:[1] ratio of the high polarity compounds, medium polarity compounds and non-polar compounds by weight.

5. The method of claim 1, wherein the composition comprises a [1]:[1]:[1] ratio of the high polarity compounds, medium polarity compounds and non-polar compounds by weight.

6. The method of claim 1, wherein the composition further comprises an effective amount of one or more chemotherapeutic agents.

7. The method of claim 1, wherein the composition is administered in combination with an immunotherapy agent.

8. The method of claim 7, wherein the immunotherapy agent is selected from the group consisting of checkpoint inhibitors, checkpoint blockers, vaccines and CAR-T cells.

9. The method of claim 1, wherein the composition is formulated for oral, buccal or transdermal administration to the subject.

10. The method of claim 1, wherein the composition comprises one or more pharmaceutical excipients selected from the group consisting of diluents, disintegrants, carriers, binders, adhesives, surfactants, lubricants, solvents, permeation enhancers, plasticizers, gelling agents, water, release agents, flavorings, sweeteners, preservatives, and mixtures thereof.

11. A method of treating oral squamous cell carcinoma in a subject in need thereof, such method comprising a step of administering a pharmaceutical composition to the subject, wherein the composition comprises: (a) one or more high polarity compounds isolated from *Curcuma longa* using a high polarity solvent system having a dielectric constant of greater than about 25 and a relative polarity value of greater than about 0.6 and selected from the group consisting of proteins, polysaccharides, and peptides; (b) one or more medium polarity compounds isolated from *Curcuma longa* using a medium polarity solvent system having a dielectric constant of about 5 to about 25 and a relative polarity value of about 0.25 to about 0.6 and selected from the group consisting of polyphenols, curcumin, demethoxycurcumin, and bisdemethoxycurcumin; and (c) one or more non-polar compounds isolated from *Curcuma longa* using a non-polar solvent system having a dielectric constant of less than about 5 and a relative polarity value of less than about 0.2 and selected from the group consisting of terpenoids, ar-turmerone, α-turmerone, and β-turmerone; wherein the composition comprises a ratio of the high polarity compounds, medium polarity compounds and non-polar compounds selected from the group consisting of about [1]:[1]:[1] by weight and about [3]:[6]:[1] by weight.

12. The method of claim 11, wherein one or more of the high polarity compounds, medium polarity compounds and non-polar compounds are micronized.

13. The method of claim 11, wherein the method increases T-cell infiltration in the oral squamous cell carcinoma tumor microenvironment.

14. The method of claim 11, wherein the composition further comprises an effective amount of one or more chemotherapeutic agents.

15. The method of claim 11, wherein the composition is administered in combination with an immunotherapy agent.

16. The method of claim 15, wherein the immunotherapy agent is selected from the group consisting of checkpoint inhibitors, checkpoint blockers, vaccines and CAR-T cells.

17. The method of claim 11, wherein the composition is formulated for oral, buccal or transdermal administration to the subject.

* * * * *